(12) United States Patent
Doucet

(10) Patent No.: US 10,444,172 B2
(45) Date of Patent: Oct. 15, 2019

(54) CHILLED MIRROR HYGROMETER

(71) Applicant: ROSCID TECHNOLOGIES, INC., Woburn, MA (US)

(72) Inventor: Donald Doucet, Woburn, MA (US)

(73) Assignee: ROSCID TECHNOLOGIES, INC., Woburn, MA (US)

( * ) Notice: Subject to any disclaimer, the term of this patent is extended or adjusted under 35 U.S.C. 154(b) by 102 days.

(21) Appl. No.: 15/349,058

(22) Filed: Nov. 11, 2016

(65) Prior Publication Data

US 2017/0138874 A1 May 18, 2017

Related U.S. Application Data

(60) Provisional application No. 62/254,985, filed on Nov. 13, 2015.

(51) Int. Cl.
*G01N 25/00* (2006.01)
*G01N 25/68* (2006.01)

(52) U.S. Cl.
CPC .................... *G01N 25/68* (2013.01)

(58) Field of Classification Search
CPC ....................................................... G01N 25/68
See application file for complete search history.

(56) References Cited

U.S. PATENT DOCUMENTS

| | | | | |
|---|---|---|---|---|
| 3,166,928 A | * | 1/1965 | Jackson | G01N 25/68 374/20 |
| 4,216,669 A | * | 8/1980 | Harding, Jr. | G01N 25/68 374/20 |
| 4,345,455 A | * | 8/1982 | Hayes, Jr. | G01N 25/68 374/20 |
| 5,816,704 A | * | 10/1998 | Campbell | G01N 25/68 374/28 |
| 2008/0169934 A1 | * | 7/2008 | Lang | G01N 33/0009 340/632 |

FOREIGN PATENT DOCUMENTS

JP   H08233809   * 9/1996   .......... G01N 21/274

* cited by examiner

*Primary Examiner* — Blake A Tankersley
(74) *Attorney, Agent, or Firm* — Lando & Anastasi, LLP

(57) ABSTRACT

A chilled mirror hygrometer may comprise a thermoelectric module, a polished mirror surface, two light emitting diodes, and a single photo-transistor or optical detector. A software controller may be employed to rapidly alternate between illuminating the two light emitting diodes. The software controller may allow the single photo-transistor or optical detector to rapidly alternate between observing the light from the first light emitting diode or the second light emitting diode. The chilled mirror hygrometer may further comprise a wand portion and an electrical housing.

16 Claims, 17 Drawing Sheets

CHILLED MIRROR HYGROMETER

CROSS-REFERENCE TO RELATED APPLICATION

This application claims the benefit of priority to U.S. Provisional Patent Application Ser. No. 62/254,985 filed on Nov. 13, 2015, the entire disclosure of which is hereby incorporated herein by reference in its entirety for all purposes.

BACKGROUND

Humidity, dew point, frost point, temperature and barometric pressure measurements play a critical role in various scientific and industrial settings, including HVAC systems, clean rooms, glove boxes, industrial processes, pharmaceutical laboratories, emissions testing, greenhouse monitoring, weather stations, as a component in precision dew point and RH generators, environmental chambers, octane measurement, shipping containers, and ground transport of humidity-sensitive foodstuffs. These industrial applications require moisture and water vapor measurement over a very wide range of concentrations, which can vary from as much as 1% to less than 1 part per million by volume, and over a large range of ambient temperatures, from as little as −100° C. to as much as 225° C. Various techniques have been employed to measure these fundamental properties of water vapor and derived moisture measurement units.

One technique used to measure humidity, dew point, frost point, temperature or barometric pressure is referred to as a "chilled mirror hygrometer." Chilled mirror hygrometers have been widely used in commercial applications since the 1960s. A schematic of a conventional chilled mirror hygrometer optical configuration is shown in FIG. 13. In a conventional chilled mirror hygrometer, a polished mirror surface is cooled through the use of a thermoelectric cooler, a Peltier stack, or through cryogenic means. The mirror surface is typically plated with a reflective and conductive material such as gold, platinum, rhodium, nickel, or chrome. A precision thermometer, such as a platinum resistance thermometer (PRT) contacts or is bonded to the polished mirror. A high intensity light-emitting diode (LED) illuminates the polished mirror surface and the amount of light that is reflected from the surface of the mirror is detected with a photo-transistor or optical detector.

Chilled mirror hygrometers measure humidity, dew point, frost point, temperature or barometric pressure by observing the temperature at which dew or frost forms on the surface of the polished mirror. When the temperature of the mirror surface is reduced below the dew or frost point by the thermoelectric cooler, moisture forms as dew or frost on the polished mirror. Because of the presence of moisture, the light hitting the polished mirror is scattered and the amount of light reflected by the mirror onto the photo-transistor or optical detector is therefore reduced. The photo-transistor or optical detector observes the reduction in light being reflected towards it by the polished mirror and the precision thermometer provides the temperature at which the reduction in reflected light occurred.

Some chilled mirror hygrometers seek to establish a condensate equilibrium at the dew or frost point temperature at the polished mirror surface. As dew or frost forms on the polished mirror surface, the light being observed by the photo-transistor or optical detector is reduced. In some chilled mirror hygrometers, this causes the cooling device to begin raising the temperature of the polished mirror surface either through a thermo optical servo system or by means of a digital controller. As the temperature on the mirror rises, the dew or frost on the polished mirror surface eventually begins to disappear, which causes the amount of light observed by the photo-transistor or optical detector to increase. This increase in observable light then causes the cooling device to begin lowering the temperature, again, either through a thermo optical servo system or by means of a digital controller. The changes in temperature and observable light during this cycle are minute and, in effect, establish a condensate equilibrium at the dew or frost point temperature at the polished mirror surface.

The precision of chilled mirrors are affected, over time, by the accumulation of dirt and other contaminants on the polished mirror surface. Chilled mirror hygrometers require access to the ambient air or an air sample in order to take measurements. These air samples often times contain dirt and other contaminants that are deposited on the chilled mirror surface. Maintaining a condensate equilibrium at the dew or frost point temperature on the polished mirror surface further encourages the accumulation of contaminants because dirt and other contaminants accumulate more readily in the presence of moisture. One solution to the accumulation of dirt is to periodically open the chilled mirror hygrometer and mechanically clean the polished mirror surface. However, this method may scratch the polished mirror surface, which causes unwanted nucleation sites to appear on the mirror surface. Furthermore, this method will not prevent accumulated dirt from affecting the measurements of the hygrometer during operation.

A variety of calibration procedures may also be used to continually recalibrate a chilled mirror hygrometer to account for the presence and buildup of dirt and other contaminants on the polished mirror. One re-calibration technique is referred to as an "automatic balancing control" or "ABC" cycle. Using this technique, the chilled mirror hygrometer is programmed to heat the polished mirror surface to a temperature well in excess of the dew point to ensure that the mirror will be dry. The hygrometer then measures the loss in reflectivity of the polished mirror surface that is attributable to contaminants, alone, and in the absence of any moisture by comparing the reflectivity of the dry, but dirty, mirror against a baseline measurement of light directly from an LED to an optical sensing circuitry. Based on this reading, the optical sensing circuitry is automatically adjusted to compensate for any loss in reflectivity that is caused by contamination on the mirror surface.

The "Programmable Automatic Contaminant Error Reduction" or "PACER" cycle also adjusts optical sensing circuitry to account for the presence of contaminants on the polished mirror surface. Unlike the ABC cycle, the PACER technique begins by first reducing the temperature of the chilled mirror below the dew point, allowing water to condense on the surface of the mirror. The condensed water then forms into puddles on the polished mirror surface. These puddles cause soluble materials to dissolve. The PACER circuit then causes the mirror to be rapidly heated to a temperature well in excess of the dew point in order to ensure that the mirror rapidly dries. The puddles that formed on the polished mirror surface rapidly shrink as the water evaporates, increasing the concentration of contaminants in the shrinking puddle and leaving behind a clean mirror surface. Eventually the puddles become so concentrated that solute begins to precipitate out in polycrystalline clusters, which remain once the mirror is completely dry. This process redistributes the salts and other contaminants so as to concentrate them in spots around the mirror as opposed to contaminating the entire mirror surface. Even on severely contaminated mirrors, the resulting reduction in reflectance is only about 15-20%. Once the polished mirror is dry, the optical sensing circuitry can also determine the resulting reduction in reflectivity resulting from the redistributed contamination and adjust its calibration accordingly.

However, neither the ABC nor the PACER cycle will completely remove the need to periodically clean the polished mirror surface. Both of these methods merely delay the need for mechanically cleaning the polished mirror, thereby reducing wear and tear and scratching of the mirror surface over the life of the chilled mirror hygrometer. Once the polished mirror becomes too scratched or damaged from repeated cleanings, either the mirror or the hygrometer must be replaced.

The LED brightness and the sensitivity of the phototransistor or optical detector can also be directly affected by several factors present within the air sample, itself, such as dirt, temperature, and moisture levels. To compensate for these additional sources of potential imprecision, chilled mirror hygrometers typically contain two pairs of LEDs and photo-transistors or optical detectors, as shown in FIG. 13. One pair of optical components is used to measure the presence of dew or frost on the polished mirror surface. The second pair of optical components is used as a reference or control to measure the effect of the air sample, itself, on the optical components in order to correct for fluctuations in the light caused by the air sample and not the presence of moisture on the polished mirror surface. However, the need for two sets of optical components requires a significant amount of space and presents challenges in small chilled mirror hygrometers. In small chilled mirror hygrometers, designers may forgo the additional precision afforded by including a control LED in order to maximize space. The additional optical components also increase the manufacturing costs for chilled mirror hygrometers.

Thus there is a need for a chilled mirror hygrometer that reduces the number of optical components required to operate a chilled mirror hygrometer. Likewise, there is a need to reduce the amount and frequency of re-calibration required to provide precise and accurate readings from a chilled mirror hygrometer.

SUMMARY

Exemplary aspects of the invention include a chilled mirror hygrometer comprising a thermoelectric module, a polished mirror, two light emitting diodes; and a single photo-transistor or optical detector. In some examples, the chilled mirror hygrometer may further comprise a fan. The chilled mirror hygrometer may further comprise a wand portion and an electrical housing, the wand portion having a distal end located away from the electrical housing and a proximal end adjacent to the electrical housing. In some examples, the wand portion may further comprise two or more cylindrical housings that may be rotatably connected such that they may be rotated to align one or more holes or openings in the two or more cylindrical housings so that the aligned holes or openings may provide access to a sample chamber, which may be located between at least one of the two light emitting diodes and the polished mirror surface. The chilled mirror hygrometer may further comprise one or more platinum resistance thermometers. In some examples, the air samples may be exposed to the sample chamber near the distal end of the wand portion when the holes or openings in the two or more cylindrical housings are misaligned. In other examples, the air samples may be exposed to the sample chamber by passing through the holes or openings in the two or more cylindrical housings when the holes or openings in the two or more cylindrical housings are aligned. Some examples may further comprise a plug, which may be inserted into the wand portion so that the sample chamber is isolated from the distal end of the wand portion. In some examples the fan may be actuated during a calibration procedure. In other examples, the fan may be actuated when the chilled mirror hygrometer is sampling an air sample.

In other examples, a chilled mirror hygrometer may include an air sampling chamber comprising a polished mirror, a first light source, a second light source, an optical detector, a thermoelectric module disposed adjacent said polished mirror, and a processor programmed with a software controller for taking air sample measurements in at least three intervals. The intervals include a first interval, wherein both of the first and the second light sources are deactivated and the optical detector is measured, a second interval, wherein the first light source is activated and the optical detector is measured, and a third interval, wherein the second light source is activated and the optical detector is measured. In some examples, the first light source is aimed at the polished mirror, such that at least a portion of the light emitted from the first light source will be received at the optical detector. In other examples, the second light source is aimed at said optical detector, such that at least a portion of the light emitted from the second light source will be received at the optical detector. The first and said second light sources may also be light emitting diodes. The chilled mirror hygrometer may further comprise one or more thermometers. Furthermore, the processor may further be programmed to measure and record the temperature during at least one of the first interval, the second interval, or the third interval. One or more thermometers may also comprise a platinum resistance thermometer. In other examples, the processor may be further configured to perform a calibration procedure, and, in some examples, the calibration procedure may be a PACER cycle or an ABC cycle. The processor may further be configured to actuate a fan, disposed within the chilled mirror hygrometer, during the calibration procedure.

Still other aspects and advantages of these examples are discussed in detail below. Any example disclosed herein may be combined with any other example in any manner consistent with at least one of the objects, aims, and needs disclosed herein, and references to "an embodiment," "some embodiments," "an alternate embodiment," "various embodiments," "one embodiment" or the like are not necessarily mutually exclusive and are intended to indicate that a particular feature, structure, or characteristic described in connection with the example may be included in at least one example. The use of such terms herein is not necessarily all referring to the same example. The accompanying drawings are included to provide illustration and a further understanding of the various aspects and examples, and are incorporated in and constitute a part of this specification.

BRIEF DESCRIPTION OF THE DRAWINGS

Various aspects of at least one example are discussed below with reference to the accompanying figures. Where technical features in the figures or detailed description are followed by reference signs, the reference signs have been included for the sole purpose of increasing the intelligibility of the figures or detailed description. Accordingly, neither the reference signs nor their absence are intended to have any limiting effect on the scope of any claim elements. In the figures, each identical or nearly identical component that is illustrated in various figures is represented by a like numeral. For purposes of clarity, not every component may be labeled in every figure. The figures are provided for the purposes of illustration and explanation and are not intended as a definition of the limits of the invention. In the figures:

DETAILED DESCRIPTION

Reference will now be made to representative examples. It should be understood that the following descriptions are not intended to limit the examples to one preferred example. To the contrary, it is intended to cover alternatives, modifications, and equivalents as may be included within the spirit and scope of the described examples as defined by the claims.

Figure 1:
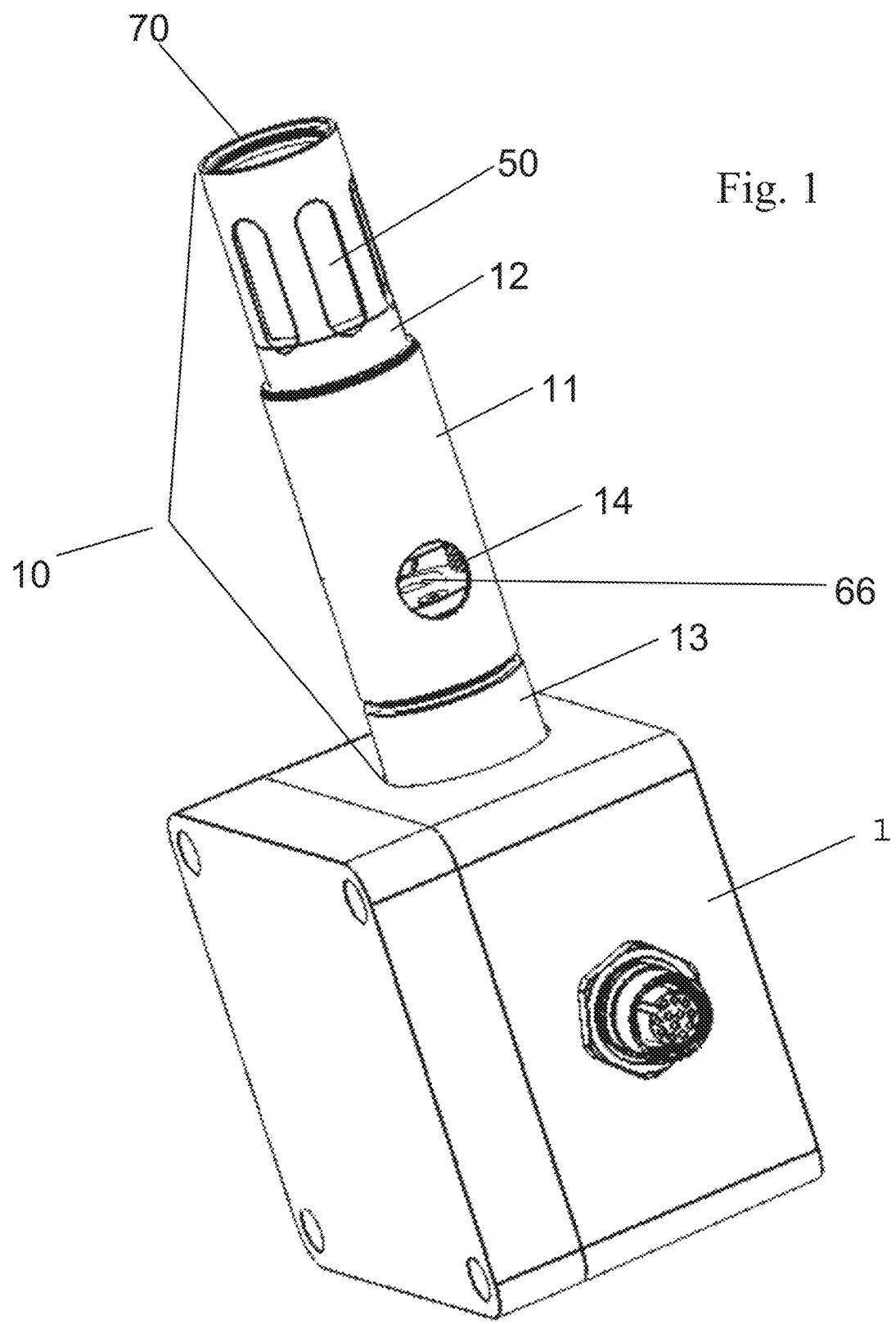
FIG. 1 is a perspective, exterior view of a chilled mirror hygrometer.

FIG. 1 is a perspective view of a chilled mirror hygrometer according to an example. In one example, the chilled mirror hygrometer may comprise an electronic housing 1 and a wand portion 10. In some examples, electronic housing 1 may contain, among other things, and the power supply for the thermoelectric cooler or Peltier stack contained within wand portion 10, circuitry for calculating additional, secondary moisture values (aside from dew point and temperature), connectors for connecting the chilled mirror hygrometer with an external user interface, and possibly connectors for sending signals to dew/frost point-sensitive industrial equipment. Wand portion 10 generally houses the operable components of the chilled mirror hygrometer, such as the mirror, LEDs, photo-transistor or optical detectors, and thermoelectric cooler or Peltier stack, as well as the circuitry that controls the LEDs, optical detector(s) and an analog-to-digital signal converter. In some examples, wand portion 10 is contained by an outer housing 11 and an inner housing 12. In some examples, outer housing 11 may be generally cylindrical and may be comprised of aluminum, stainless steel, plastic, ultem plastic or polyetherimide. Outer housing 11 serves as a protective sleeve over inner housing 12 and the internal components of the chilled mirror hygrometer. Inner housing 12 may be formed of the same or similar material and is also generally cylindrical in some examples. The external diameter or width of inner housing 12 should match or be slightly less than the internal diameter or width of outer housing 11 so that inner housing 12 may fit within outer housing 11. Outer housing 11 and inner housing 12 may be connected such that inner housing 12 may snap into outer housing 11. In some examples, this may be accomplished by placing a small tongue on the exterior of inner housing 12 and a small, corresponding groove on the outer housing 11 or by using any other suitable means as are known to those of ordinary skill in the art.

Sampled air may be drawn into distal tip 70 of wand portion 10, and pass into inner housing 12 and outer housing 11 to be analyzed by the hygrometer, as described below. The distal end of wand portion 10 may have an opening through which sampled air may pass. Distal tip 70 may also include one or more perforations, to allow the passage of sampled air into wand portion 10. One or more filters 50 may be inserted into the inner housing 12 at distal tip 70 so as to filter the sampled air and reduce the amount of potential contaminants entering the wand portion 10 and sample chamber 66. Filter 50 may comprise any filter media suitable for filtering sampled air, as is known to one of ordinary skill in the art, such as a foam filter, a cloth filter, or a metal mesh filter. In some examples, filter 50 may comprise a stainless steel porous media, which may be cut from bar stock to a specified measurement. A course filter may be used in applications where larger contaminants are anticipated, whereas finer filters may be used in applications with smaller contaminants.

Multiple filter layers may be used, with varying levels of coarseness for the filters. In such examples, the filter layers should be arranged with the coarsest filters layers mounted externally and the finer filter layers mounted internally. Filter 50 may range from 5 to 100 micrometers porosity, but may range from 60 to 100 micrometers in some applications. The porosity and filter media for filter 50 may be altered to suit the needs of any given application. In some examples, the outer diameter or dimension of filter 50 may be sized to match the internal diameter or dimension of inner housing 12 in order to form a close fit when filter 50 is inserted into the top end of inner housing 12. In some examples, filter 50 may be retained within inner housing 12 through the use of one or more adhesives or a fastener. In yet further examples, filter 50 may be retained within a metal or plastic ring 51 that may be inserted within inner housing 12 and be located between filter 50 and inner housing 12 in order to provide a space between filter 50 and inner housing 12. In some examples, the chilled mirror hygrometer may be configured for use as a duct-mounted unit, as discussed below.

Figure 2:
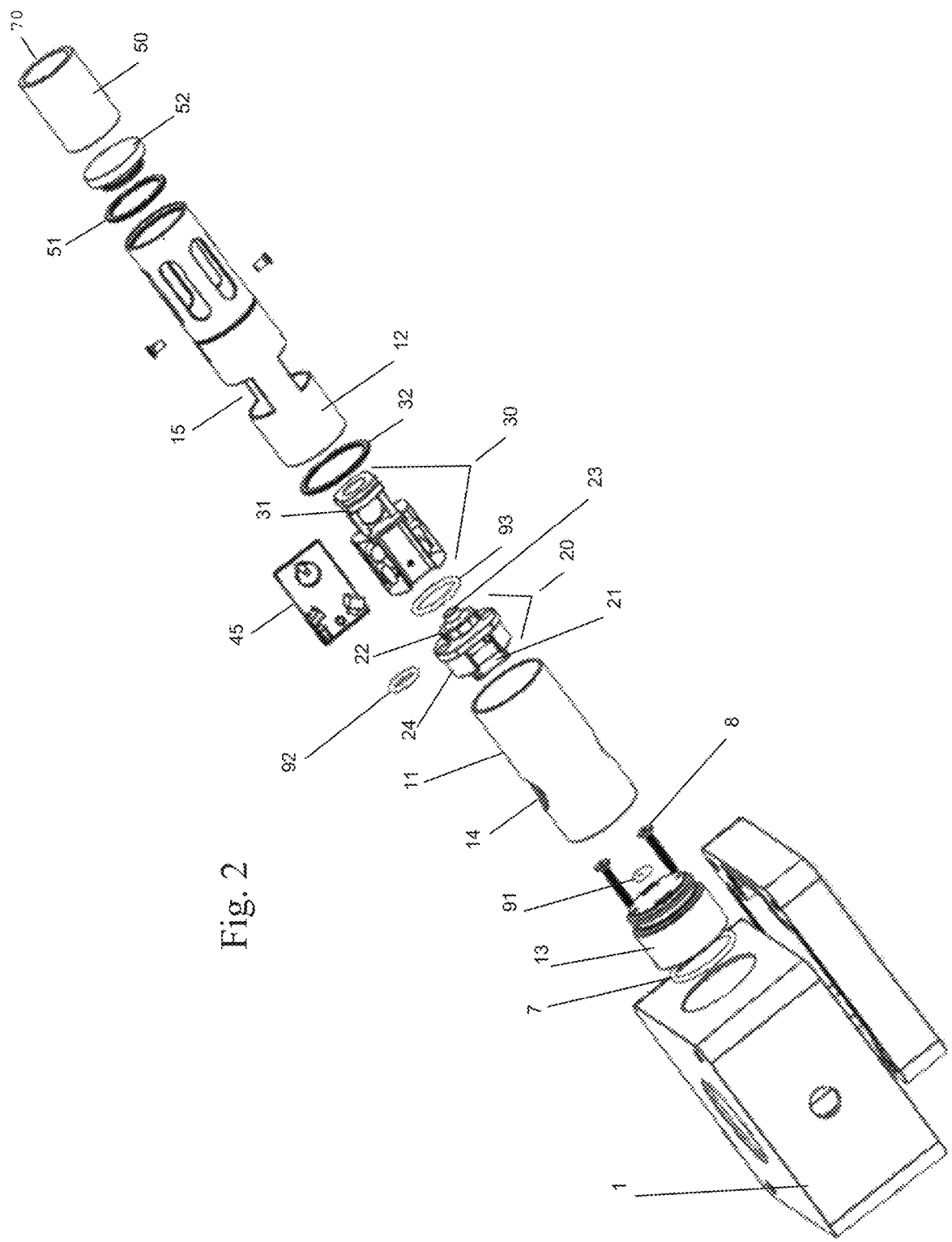
FIG. 2 is an exploded view of a chilled mirror hygrometer.
Figure 3:
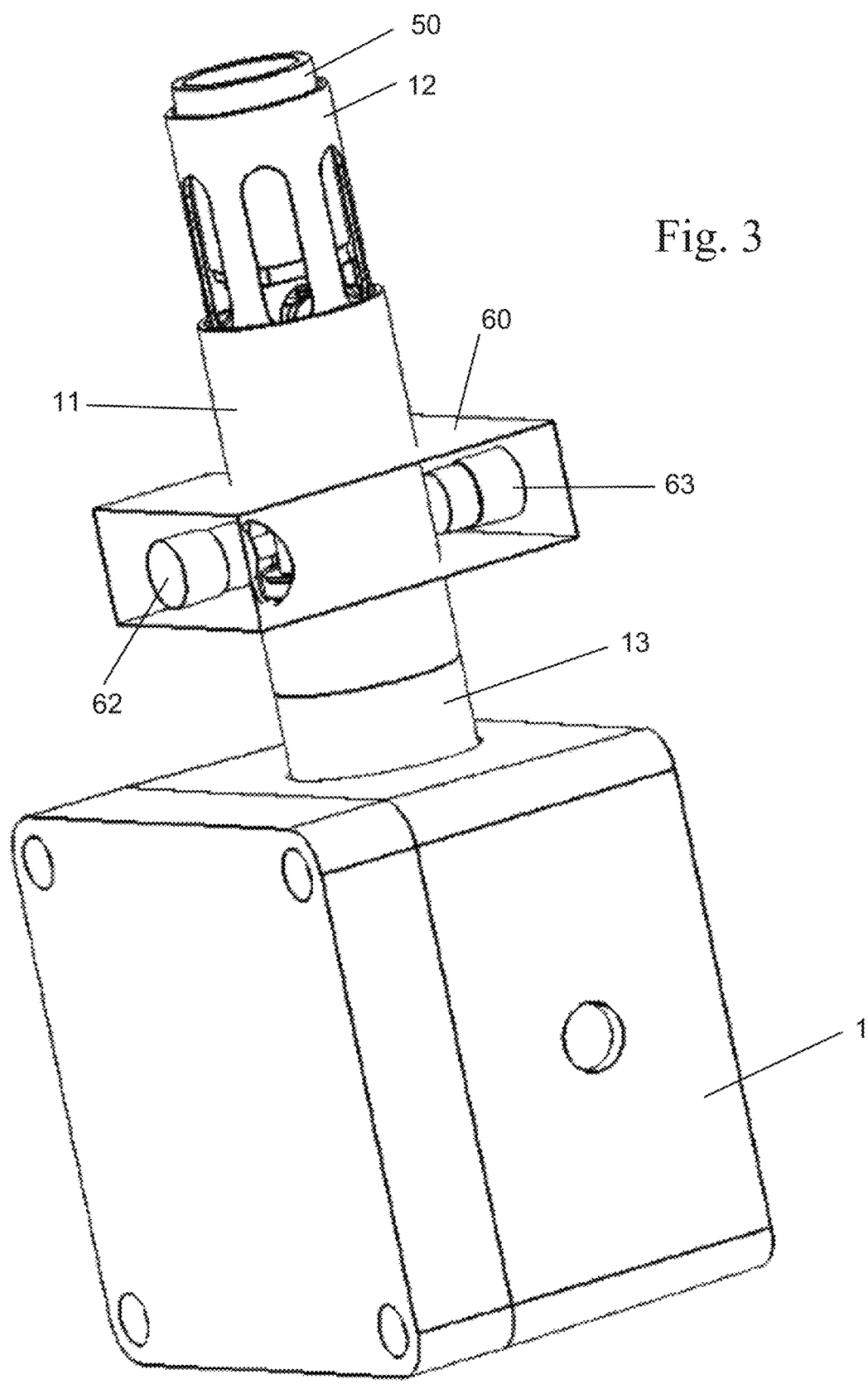
FIG. 3 is a perspective, exterior view of a chilled mirror hygrometer.

FIG. 2 is an exploded view of the chilled mirror hygrometer, which shows, among other things, how inner housing 12 and outer housing 11 can be configured to provide for an alternative path for sampled air to enter wand portion 10. In some examples, inner housing 12 and outer housing 11 are sized and arranged to be rotatably connected. This allows the user to rotate outer housing 11 such that hole 14 on outer housing 11 may align with opening 15 on inner housing 12. This configuration allows for direct access to sample chamber 66, as shown for example in FIG. 1, through hole 14 and opening 15, which holes are both shown in FIG. 2, when properly aligned. In this configuration, the user may also attach sample attachment 60, which may be used to direct samples into and out of sample chamber 66, as shown, for example in FIGS. 3-6. In other examples, inner housing 12 and outer housing 11 are in a closed position, such that hole 14 and opening 15 are misaligned. In this configuration, samples are drawn into sample chamber 66 from distal tip 70 of wand portion 10. In some examples there may be no need for separate internal and external housings and in those examples, one or more housings may be omitted or they may be integrally formed with one another.

Figure 4:
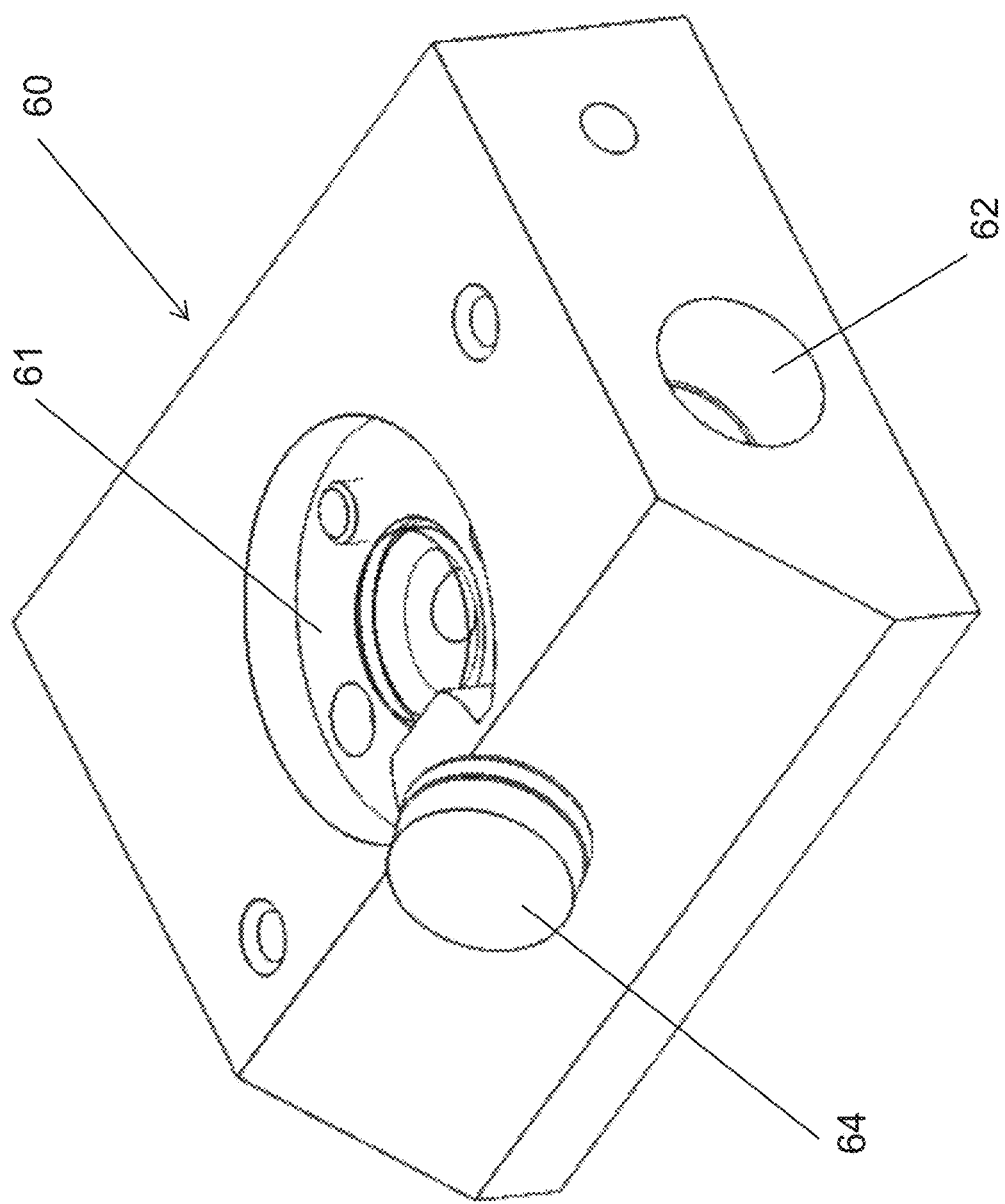
FIG. 4 is a perspective view of a sample attachment portion.
Figure 5:
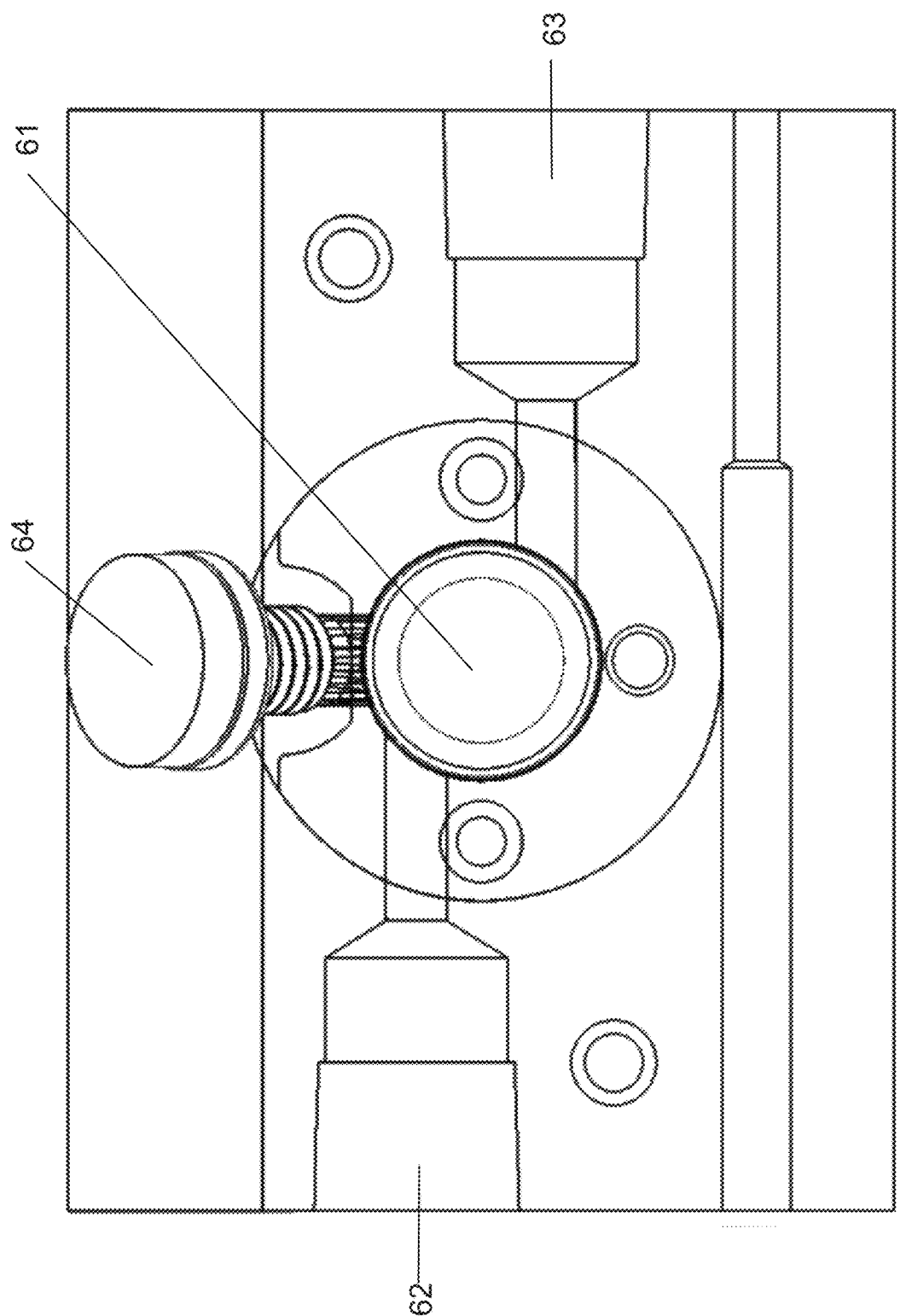
FIG. 5 is a cross-sectional view of a sample attachment portion.

Referring now to FIGS. 3-6, sample attachment 60 may be installed onto wand portion 10 by inserting the wand portion through hole 61, as shown, for example, in FIG. 4, which may be generally at the center of sample attachment 60. Sample attachment 60 may then be lowered onto the wand portion until holes 62 and 63 (shown in FIG. 5) align with hole 14 and opening 15 of inner housing 12 and outer housing 11, as shown, for example, in FIG. 3. Sample attachment 60 may align with external housing 11 and inner housing 12 by any suitable means as are known in the art. In one example, screw 64 may attach sample attachment 60 to external housing 11 or inner housing 12, which may have a threaded hole for receiving screw 64. In some examples, a plug 52, as shown in FIG. 2, may also be installed within inner housing 12 or outer housing 11 in order to stop ambient air from traveling through the wand portion.

Figure 6:
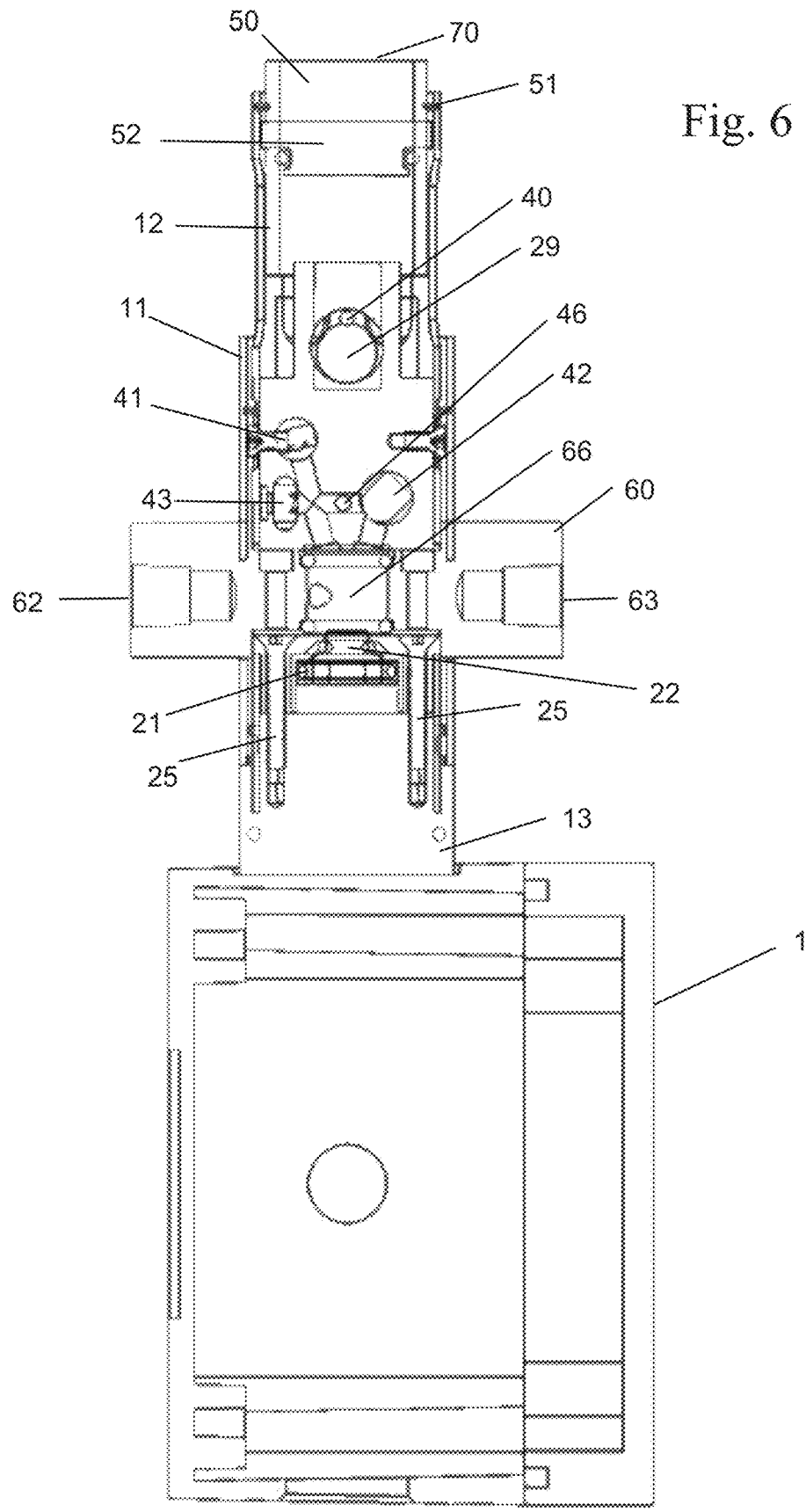
FIG. 6 is a cross sectional view of a chilled mirror hygrometer.

As shown, for example, in FIG. 6, once sample attachment 60 is attached, sampled air may be forced through hole 62 in sample attachment 60 and through hole 14 and opening 15 in inner housing 12 and outer housing 11 and into sample chamber 66. In some examples, tubing may be connected to holes 62 and 63, through the use of fittings as is known to those of skill in the art, in order to draw an air sample from a container into sample chamber 66, which tubing may be ¼ inch rubber tubing or any other suitable tubing as is known in the art. In sample chamber 66, the air sample may be analyzed as described below, before passing out of sample chamber 66 and through hole 63. This configuration is useful for analyzing an isolated sample of air that has been isolated from the ambient air, such as from a sintering oven, carbonizing furnace, gas purity testing, or any other environmentally sealed batch of air.

Referring again to FIG. 2, the general arrangement of the internal components of the chilled mirror hygrometer may be seen. At the base of the chilled mirror hygrometer, external housing 11 may be inserted into and/or fastened to base member 13. Base member 13 may comprise a flanged, cylindrical portion for connecting external housing 11 to electronic housing 1. For example, the upper, flanged portion of base member 13 may be threaded so that external housing 11 may be twisted onto base member 13. Likewise, the interior of the bottom portion of external housing 11 may also be threaded in order to fasten external housing 11 to base member 13. In some examples, an o-ring 7 may be placed on the upper, flanged portion of base member 13 to ensure a tight fit between base member 13 and external housing 11. In yet further examples, adhesives may also be applied between base member 13 and external housing 11 during coupling. Base member 13 may be fastened to electronic housing 1 using any suitable means, as are known to those of ordinary skill in the art. In some examples, base member 13 may be fastened to electronic housing 1 by using one or more screws 8, as shown, for example, in FIG. 2. In some examples, an o-ring and/or adhesives may also be applied between base member 13 and electrical housing 1 prior to coupling. In some examples, base member 13 may have one or more holes passing through base member 13 so that one or more electrical wires and/or platinum resistance thermometers may pass from wand portion 10 into electrical housing 1.

Figure 7B:
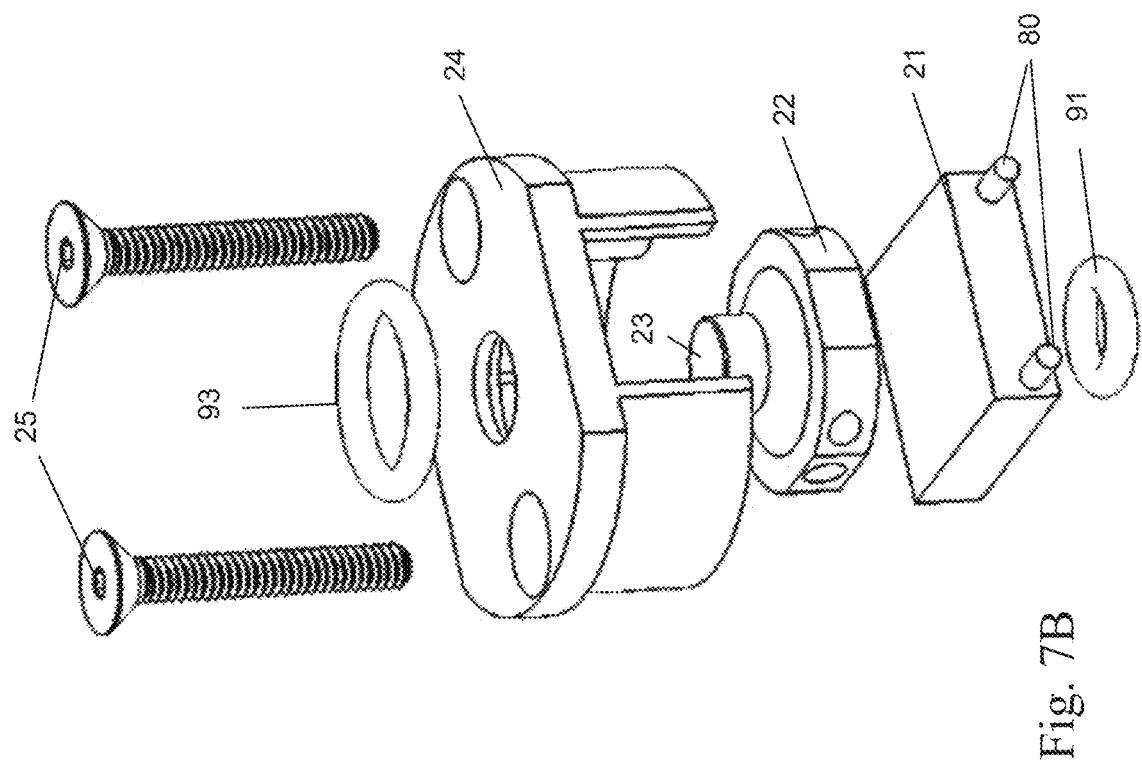
FIG. 7B is an exploded view of a chilled mirror assembly within a chilled mirror hygrometer.
Figure 7A:
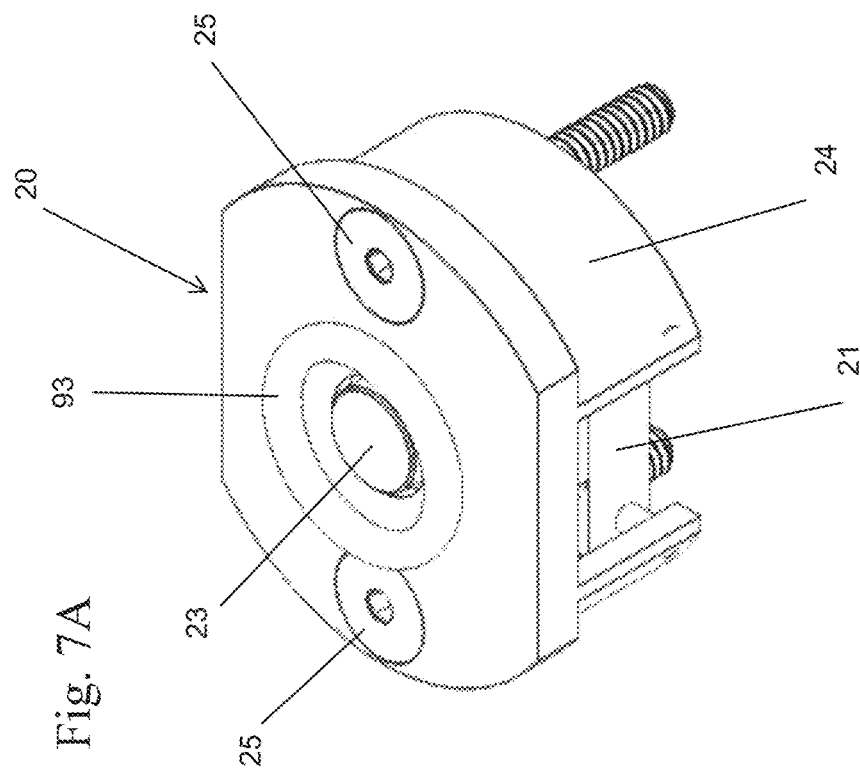
FIG. 7A is a top perspective view of a chilled mirror assembly within a chilled mirror hygrometer.

FIGS. 7A and 7B provide a detailed view of chilled mirror assembly 20 in both an assembled and exploded view, respectively. In some examples, chilled mirror assembly 20 may be located within internal housing 12 and external housing 11 and generally on top of base member 13. Chilled mirror assembly 20 may comprise one or more thermoelectric modules 21 for cooling and heating mirror block 22, and polished mirror 23. Potting shell 24 may also be located around thermoelectric module 21 and mirror block 22. In some examples, thermoelectric module 21 may be a Peltier cooler capable of chilling the surface of polished mirror 23 to −25° C. below and heat it to +50° C. above the ambient air temperature. In other examples, the thermoelectric module 21 may be capable of chilling the surface of polished mirror 23 to −45° C. below and heat it to +75° C. above the ambient air temperature.

Figure 9:
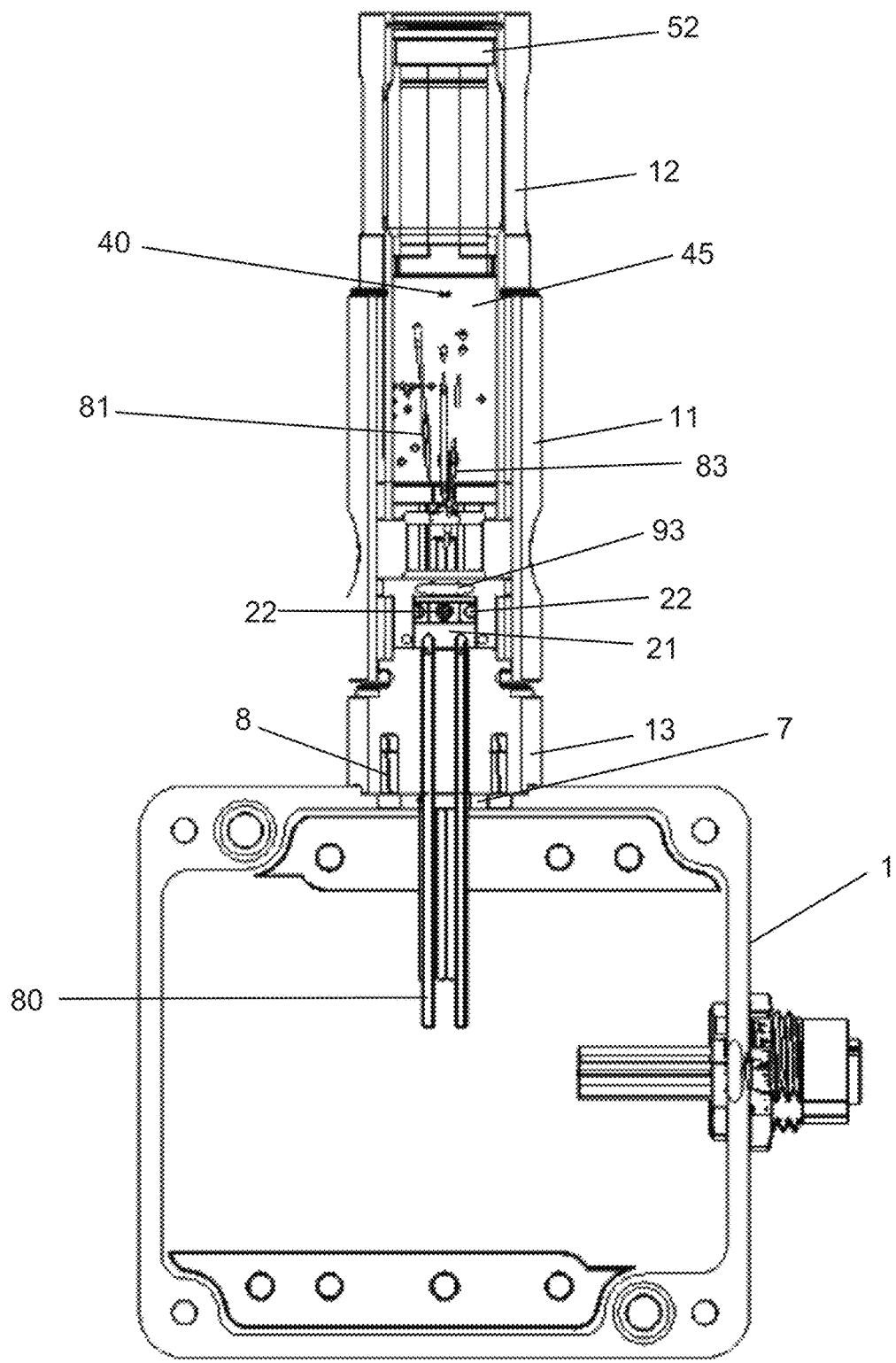
FIG. 9 is a cross sectional view of a chilled mirror hygrometer.

FIG. 9 shows a cross sectional view of a chilled mirror hygrometer, including the location of several PRTs and power supply wires within the device. In some examples, the thermoelectric module may require approximately 3 amperes and approximately 1-5 volts of electricity, which may be supplied by wires 80, which attach to the thermoelectric module 21 and connect to a power supply through electronic housing 1. A platinum resistance thermometer 81 may also be attached to thermoelectric module 21 and circuit board 45 at the other end. PRT 81 is preferably a four-wire PRT but may also be a three-wire PRT in other examples of the invention.

Referring again to FIGS. 7A and 7B, mirror block 22 may be located directly on top of thermoelectric module 21. In some examples, mirror block 22 may serve as a surface upon which a separate polished mirror 23 may be mounted. In other examples, mirror block 22 may be a monolithic mirror block and may have a polished mirror surface integrally formed at its top. Ideally, mirror block 22 should be formed of a reflective and/or highly thermally conductive material, such as copper, gold, silver, or platinum, although other materials may also be suitable as is generally known in the art. Mirror block 22 should provide a low thermal resistance path from the thermoelectric module to the polished mirror surface.

The top surface of mirror block 22 may protrude through a hole in the center of potting shell 24. A polished mirror 23 may be adhered to the top surface of mirror block 22. Alternatively, the top of mirror block 22 may be coated with a highly reflective material, for example, by electroplating gold, rhodium, platinum, or chrome. In other examples the polished mirror surface may be applied by electroless nickel plating. The polished mirror may comprise a thin layer of any highly reflective, thermally conductive material, such as gold, platinum, rhodium, chrome, as is known to one of ordinary skill in the art. Alternatively, polished mirror 23 may be prepared by cutting a thin slice from a piece of bar stock, adhering it to the top surface of the mirror block 22, and polishing it to maximize reflectivity.

The thermoelectric module 21 and mirror block 22 may be retained within potting shell 24. Potting shell 24 may hold thermoelectric module 21 and mirror block 22 in place and may be shaped and dimensioned internally to receive thermoelectric module 21 and mirror block 22. Potting shell 24 may also be filled with potting compound sufficient to provide adequate thermal insulation to the components of chilled mirror assembly 20 and to avoid unwanted water infiltration. Any suitable potting compound may be used, as are known to those of skill in the art. In some examples, a urethane foam or a closed cell foam may be used. In some examples, an o-ring 92 (see FIG. 2) may also be placed between thermoelectric module 21 and the underside of the top of potting shell 24 so as to improve thermal insulation and stop any unwanted water infiltration into potting shell 24. In some examples, an o-ring 91 may be placed below thermoelectric module 21 in order to provide push-back against potting shell 24 when potting shell 24 is fastened to base member 13. In some examples, another o-ring 93 may be placed on top of potting shell 24 to provide for an airtight seal within sample chamber 66. A platinum resistance thermometer 83 may also be attached to the mirror block 22 at one end and, in some examples, may be attached to circuit board 45 at the other end, as shown, for example in FIG. 9. In some examples, chilled mirror assembly 20 may be fastened to base member 13 by one or more screws 25 passing through potting shell 24 as shown, for example, in FIG. 7B. In other examples, potting shell 24 may be fastened to base member 13 using any suitable means known to one of ordinary skill in the art, including adhesives, soldering, or integrally forming potting shell 24 with base member 13.

Referring again to FIG. 2, the chilled mirror hygrometer may contain an optical assembly 30, which may be located above chilled mirror assembly 20. Optical assembly 30 may include an optical housing 31, which is mounted within outer housing 11 and inner housing 12.

FIGS. 8A-8E provides a detailed view of the assembled optical assembly 30. In some examples, optical housing 31 may be fastened to inner housing 12 by screwing it into place using screws 38, as shown, for example, in FIGS. 8A and 8C. Alternatively, optical housing 31 may be mounted within inner housing 12 through any suitable means for fastening, as is known to one of ordinary skill in the art, including adhesives, soldering, welding, and/or integrally forming optical housing 31 with inner housing 12. In some examples, optical housing 31 may also be sized and dimensioned to meet the internal diameter of inner housing 12 in order to create a close fit between optical housing 31 with inner housing 12. In yet further examples, a retaining ring 32 may also be placed around housing 31 to keep the location of optical housing 31 fixed within inner housing 12, as shown for example in FIG. 8A. The external diameter of retaining ring 32 may match the internal diameter of inner housing 12. The internal diameter of retaining ring 32 may match the outer dimensions of optical housing 31 in order to ensure a close fit. In some examples, optical housing 31 is substantially enclosed, as shown, for example, in FIG. 8E.

Figure 8A:
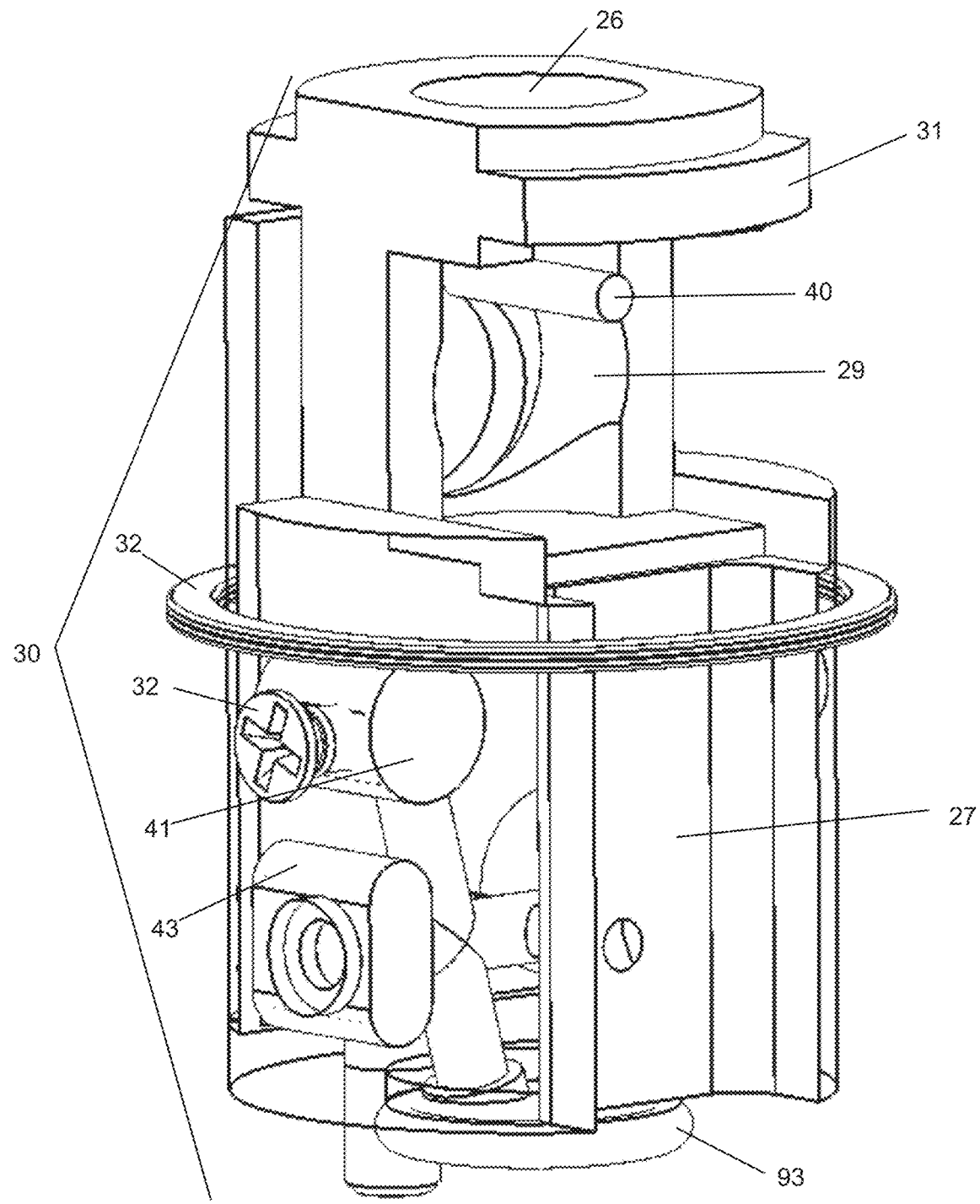
FIG. 8A is a left perspective view of an optical assembly within a chilled mirror hygrometer.
Figure 8B:
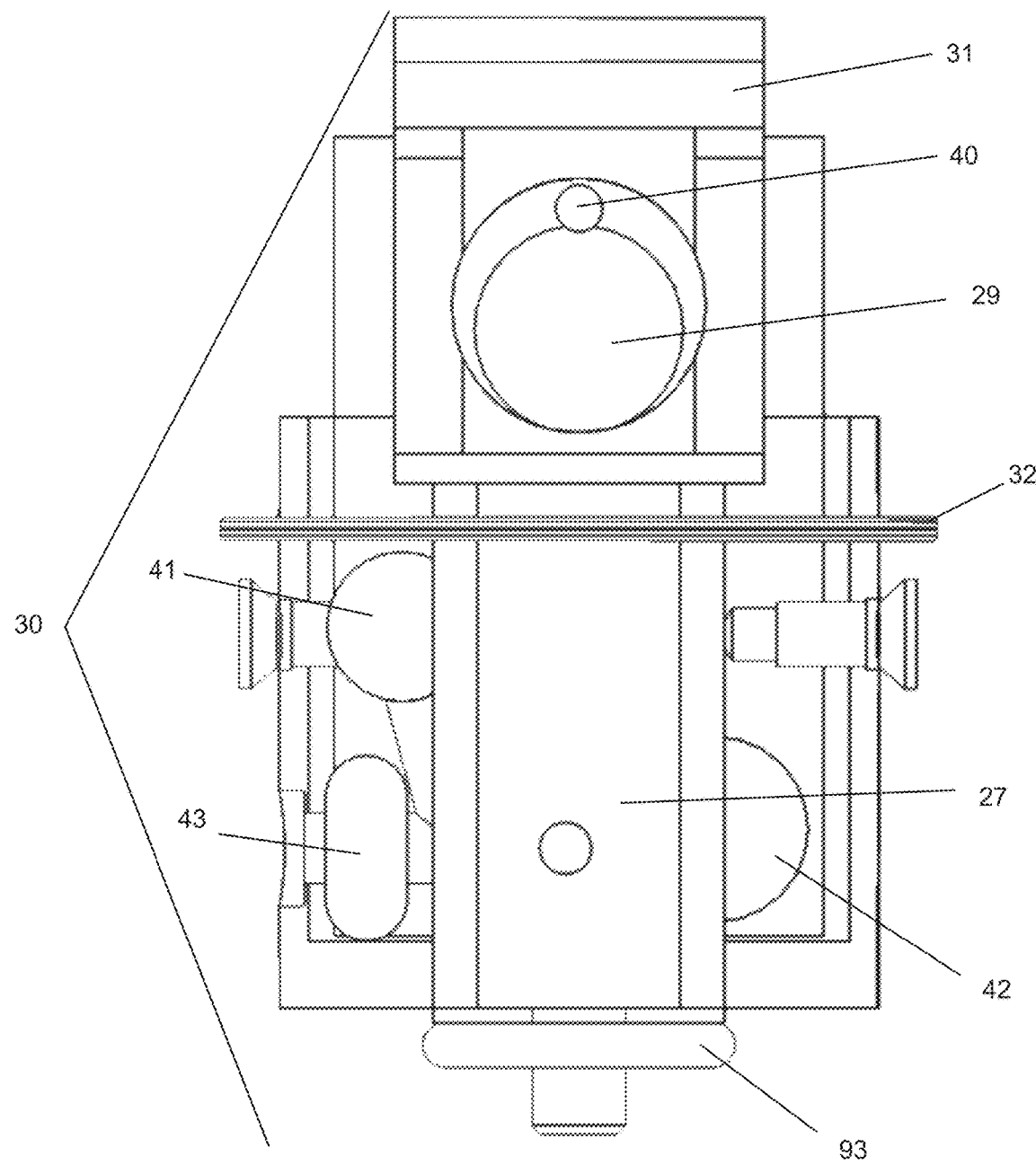
FIG. 8B is a front view of an optical assembly within a chilled mirror hygrometer.
Figure 8C:
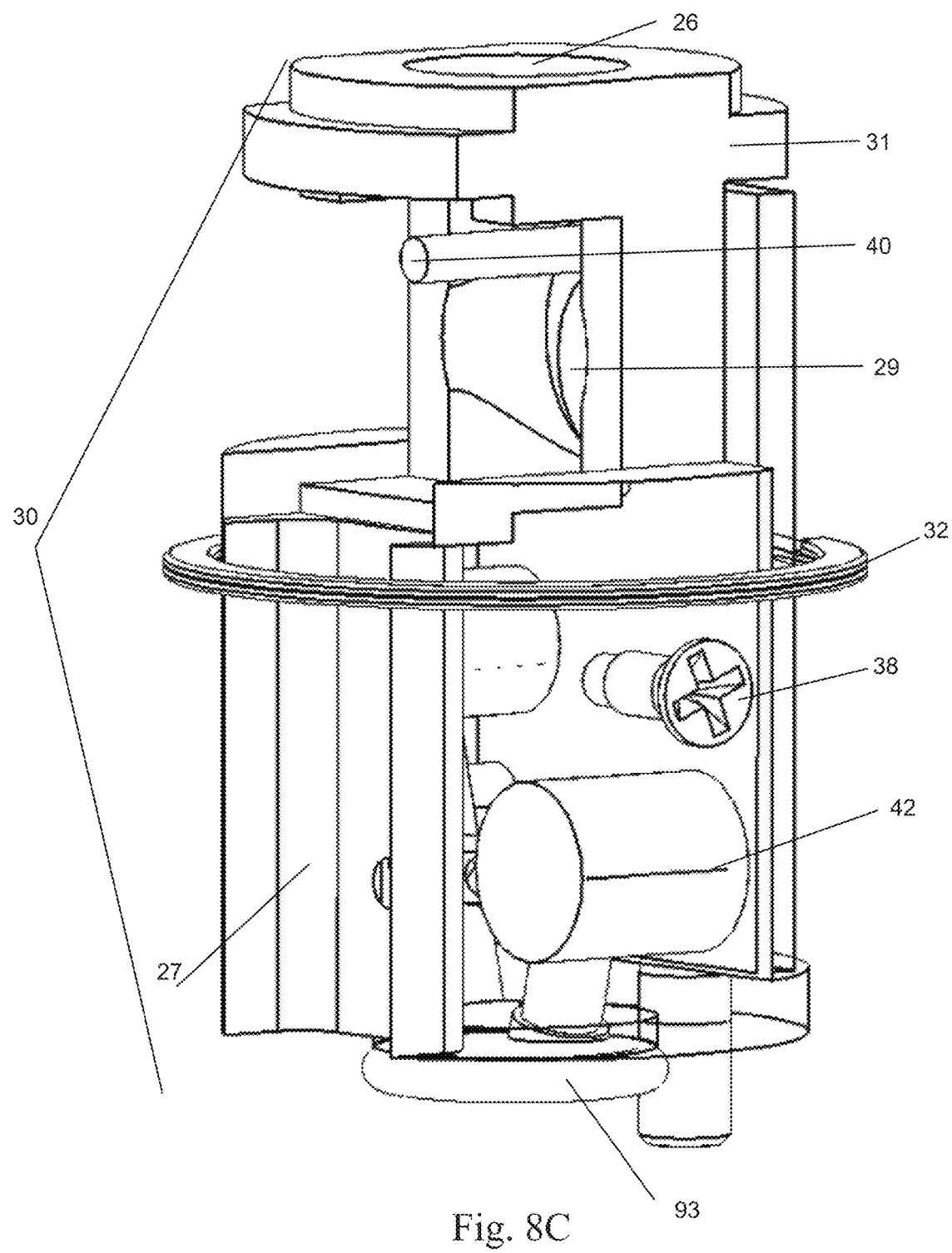
FIG. 8C is a right perspective view of an optical assembly within a chilled mirror hygrometer.
Figure 8D:
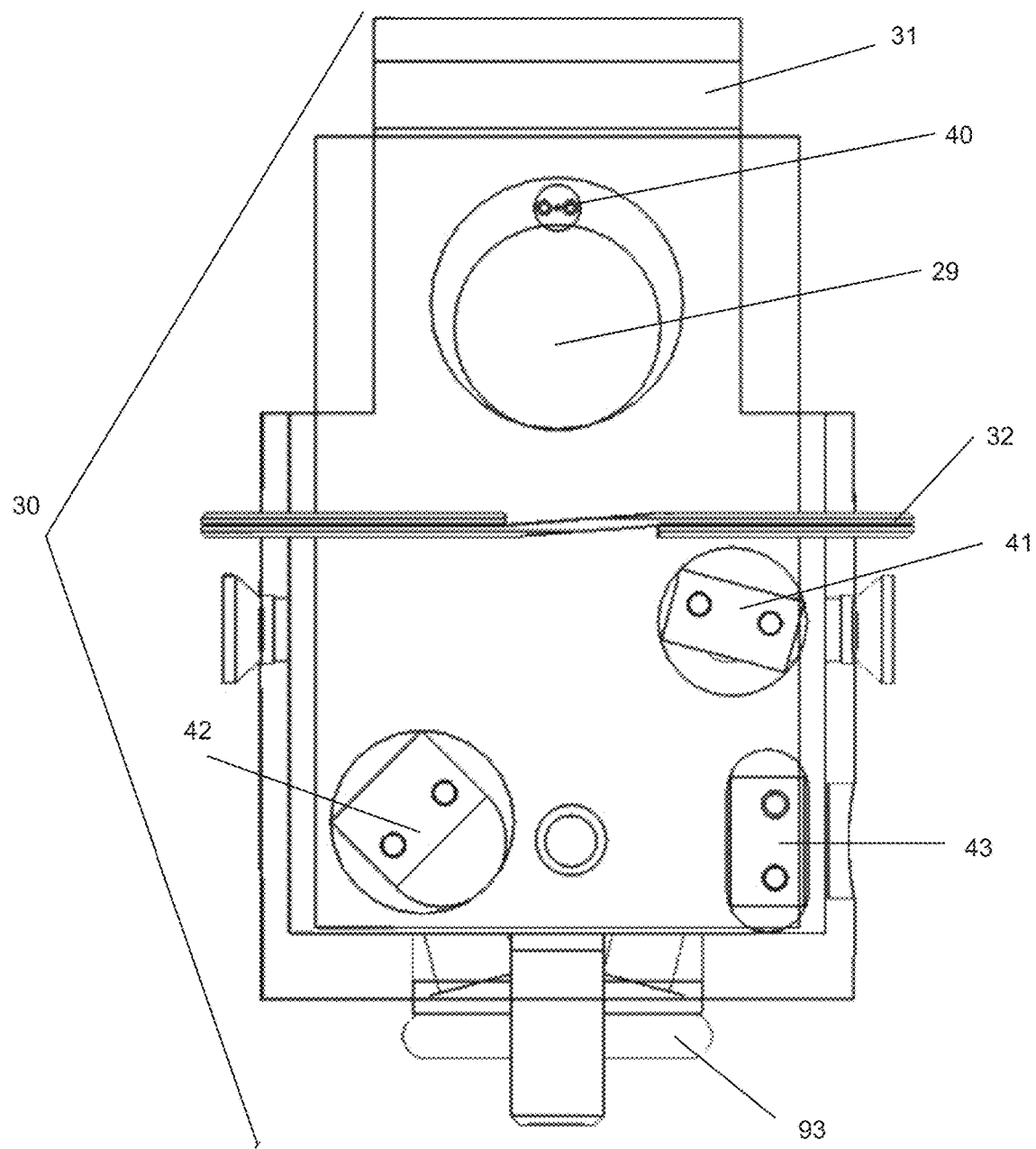
FIG. 8D is a rear view of an optical assembly within a chilled mirror hygrometer.
Figure 8E:
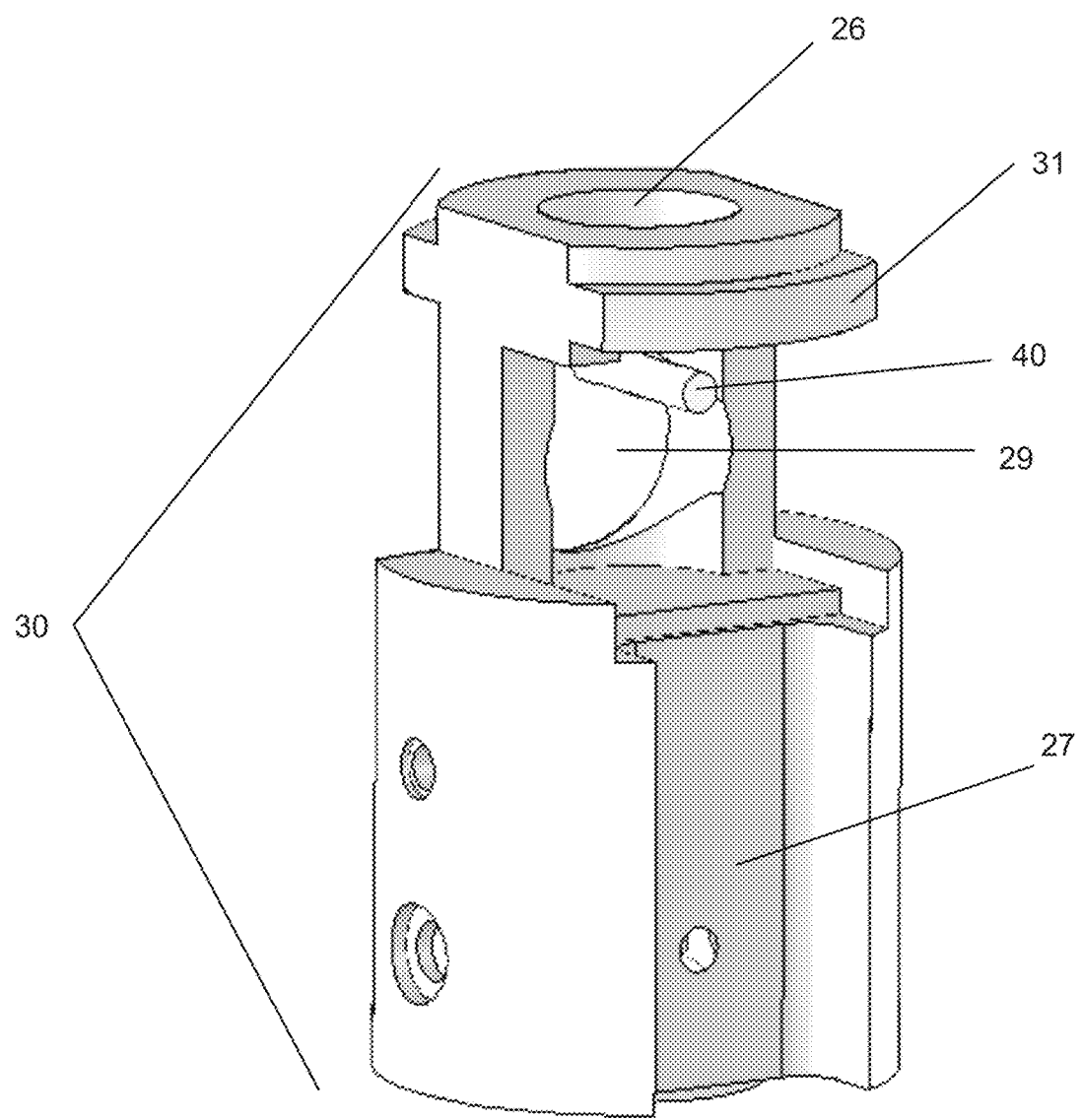
FIG. 8E is an external view of an optical housing within a chilled mirror hygrometer.

In other examples, optical housing 31 may include open or cutout portions that allow ambient air flow from the top end of wand portion 10 down through the optical housing 31, and into contact with polished mirror 23. For example, as shown in FIG. 8E, the optical housing 31 may include a top hole 26, which may receive ambient air samples entering the top end of wand portion 10. Ambient air may pass through top hole 26 to allow ambient air to reach polished mirror 23. In some examples, ambient air may also pass through recessed portion 27 in order to reach polished mirror 23.

In some examples, a miniature fan 28 may also be employed within optical housing 31 or elsewhere within the hygrometer, to aid the movement of ambient air from the top end of wand portion 10 to polished mirror 23. In such examples, optical housing 31 may include a second recessed portion 29 for receiving miniature fan 28 as shown, for example, in FIG. 8E. Miniature fan 28 may be activated when the hygrometer is configured to draw sampled air from the distal tip 70 of the wand portion 10 into sample chamber 66 for analysis, as described below. In some examples, air may not be able to flow in a straight path from distal tip 70 into sample chamber 66, and may be required to change directions one or more times in order to travel around various components within the wand, such as optical housing 31, for example. In such examples, miniature fan 28 may encourage the lateral redirection of airflow as the sampled air travels around such internal obstructions. For example, in one example, miniature fan 28 encourages ambient air to turn approximately 90 degrees as it passes from top hole 26 and down into recessed portion 27. In some examples, a platinum resistance thermometer 40 may also be located within second recessed portion 29 in order to measure the temperature of the ambient air being sampled. Platinum resistance thermometer 40 may also be connected to circuit board 45 for signal processing. In some examples, the power for fan 28 may be supplied by the optics circuitry.

In other examples, the miniature fan 28 may also be actuated as part of the calibration procedures employed when the chilled mirror hygrometer is initialized. For example, in some examples, the polished mirror 23 may be heated as part of an "ABC" or "Pacer" cycle. The chilled mirror hygrometer may include a software controller that may be programmed to actuate fan 28, once the chilled mirror surface has completed the heating portion of the ABC or PACER cycle. In such examples, a software controller may be programmed to accelerate fan 28 to its highest operating speed in order to blow at least a portion of the excess contaminants or polycrystalline clusters that formed during the heating cycle off of polished mirror 23. This additional step of blowing ambient air onto polished mirror 23 may significantly improve the reflectivity of polished mirror 23, increasing both the longevity of the polished mirror and the precision of the chilled mirror hygrometer. In other examples, the software controller may be programmed to accelerate fan 28 to its highest operating speed while polished mirror 23 is being heated, so as to aid in the evaporation process and encourage the formation of the polycrystalline clusters.

Figure 10:
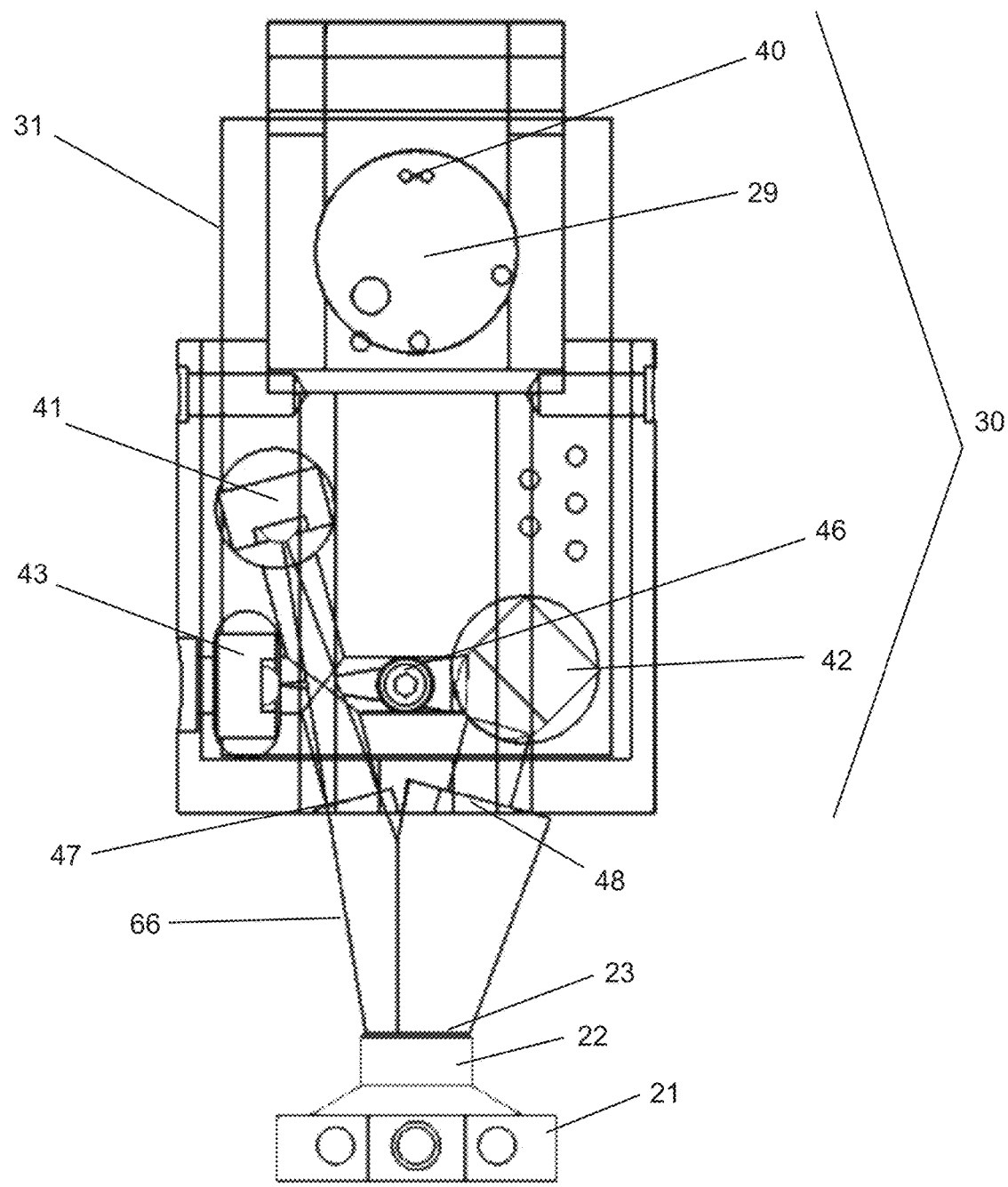
FIG. 10 is a cross-sectional view of an optical and chilled mirror assemblies within a chilled mirror hygrometer.
Figure 12B:
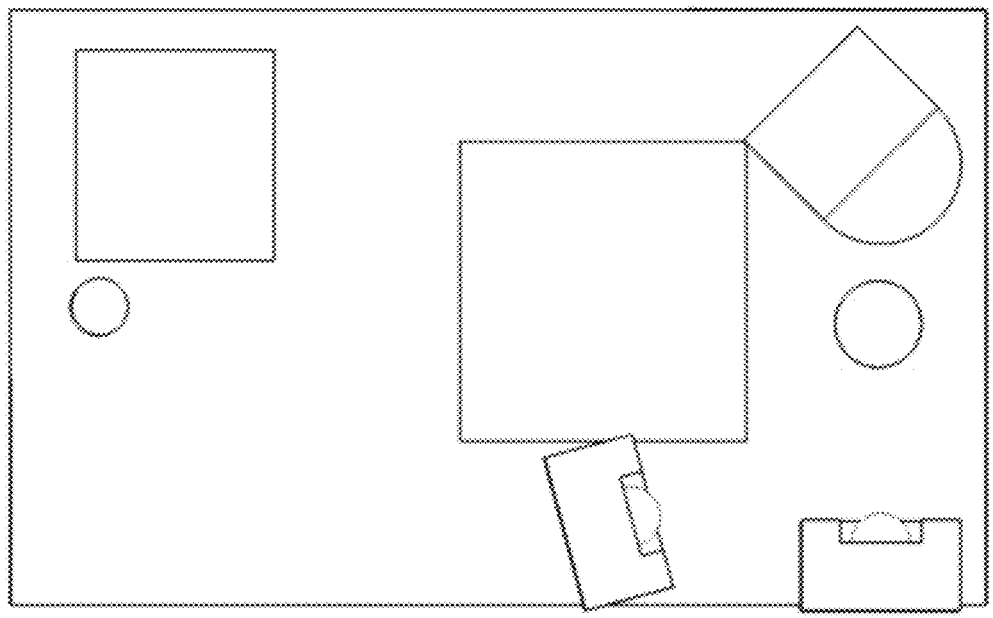
FIG. 12B is a front view of an optical circuit board within a chilled mirror hygrometer.
Figure 12A:
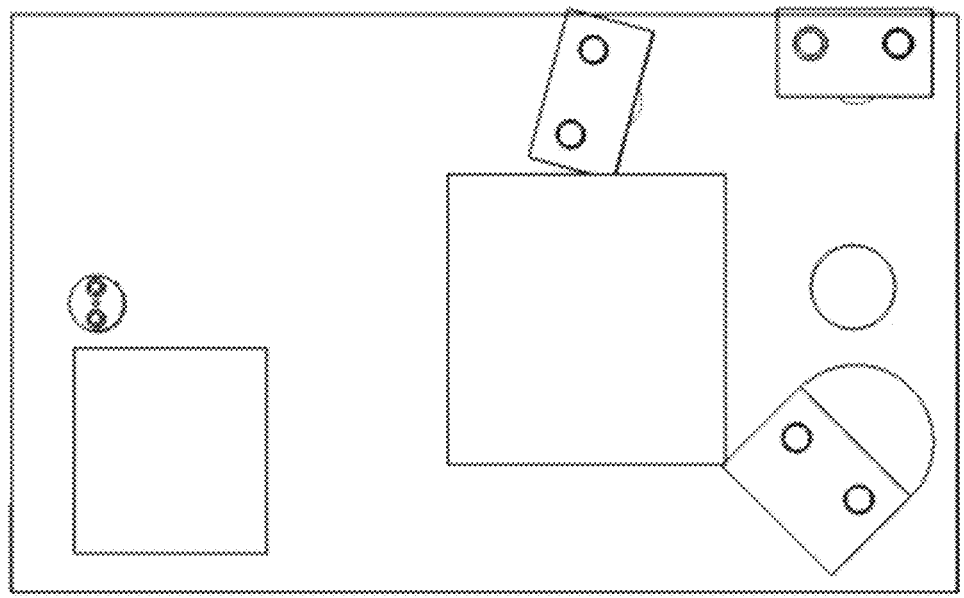
FIG. 12A is a rear view of an optical circuit board within a chilled mirror hygrometer.
Figure 13:
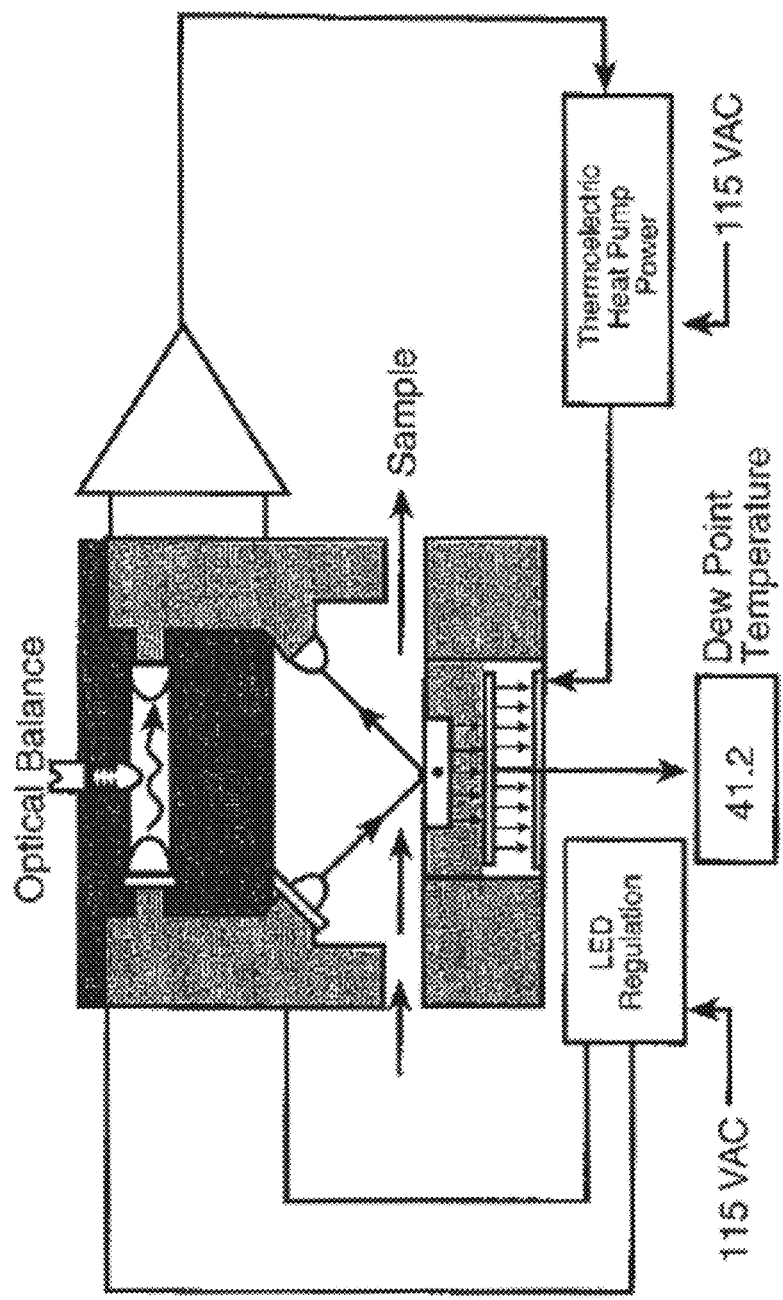
FIG. 13 is a schematic showing a typical configuration within a chilled mirror hygrometer.

FIG. 10 shows a cross-sectional view of optical assembly 30, including the optical components of the chilled mirror hygrometer. In some examples, the optical components of a chilled mirror may include a first light-emitting diode (LED) 41 that illuminates the surface of polished mirror 23 and a photo-transistor or optical detector 42 that measures the intensity of the light that is reflected by polished mirror 23. A second LED 43 may be located horizontally across from photo-transistor or optical detector 42 and may shine a light directly towards photo-transistor or optical detector 42, which measures the intensity of the light being emitted by second LED 43 in order to measure the effect of the ambient air on the transmission of the light. This second measurement allows the chilled mirror hygrometer to control for the light distortion being caused by the ambient air, and not caused by the presence of moisture or contaminants on the surface of polished mirror 23. In one example, a single photo-transistor or optical detector 42 is used to measure the intensity of the light from both first LED 41 and second LED 43. However, in other examples, a second photo-transistor or optical detector 44 may be employed to measure the intensity of the light emitted only by second LED 43 using a prior art configuration of LEDs and optical detectors, as shown, for example, in FIG. 13. In some examples, the optical components, such as first LED 41, second LED 43, photo-transistor or optical detector 42, and second photo-transistor or optical detector 44 are substantially enclosed within optical housing 31, as shown, for example, in FIGS. 8A-8C, and 8F. Enclosing the optical components in this manner may help to keep the optical components from being contaminated by dirt, thereby affecting their performance. In some examples, the optical components may be mounted on circuit board 45, as shown, for example, in FIGS. 12A, 12B, and 8D.

In one example, the optical components may be mounted and arranged within optical housing 31 such that first LED 41 may illuminate polished mirror 23, which reflects at least a portion of the light onto photo-transistor or optical detector 42, as shown, for example, in FIG. 10. Second LED 43 may be mounted and arranged within optical housing 31 such that it directly illuminates photo-transistor or optical detector 42, as shown, for example, in FIG. 10. Photo-transistor or optical detector 42 should have a half power angle sufficient to provide a reliable reading from two distinct light sources within optical housing 31. In some examples, photo-transistor or optical detector 42 may have a half power angle of at least 60. A shutter 46 may be located between second LED 43 and photo-transistor or optical detector 42 and may be adjusted to control the intensity of the light being received by photo-transistor or optical detector 42 from second LED 43, in order to avoid saturating photo-transistor or optical detector 42 with the light produced from second LED 43. This adjustment may be made during the manufacturing process of the chilled mirror hygrometer and may not need to be readjusted thereafter.

FIG. 10 shows how sampled gas may be analyzed within sample chamber 66 in one example. During typical operation, first LED 41 may be activated to produce a light source. As shown, for example, in FIG. 10, the light emitted from first LED 41 may pass through a first aperture 47, thereby focusing the beam of light such that substantially all light is emitted onto polished mirror 23. Polished mirror 23 then reflects at least a portion of the light. In some examples, after being reflected off of polished mirror 23, the light passes through a second aperture 48, thereby reducing the amount of light exiting sample chamber 66. This reduction in light hitting the photo-transistor or optical detector 42 enhances the signal quality by reducing unnecessary noise. Photo-transistor or optical detector 42 then may register the magnitude of light being reflected from polished mirror 23 in the absence of any dew or frost.

In order to reach the dew or frost point, thermoelectric module 21 may then begin cooling mirror block 22 and polished mirror 23 until frost or dew begins to form on the surface of polished mirror 23 through condensation. The presence of the frost or dew on the surface of polished mirror 23 causes the light being reflected by polished mirror 23 to be further refracted, thereby reducing the magnitude of light being detected by photo-transistor or optical detector 42, which registers the reduction in the amount of light being received. Platinum resistance thermometer 83, which is connected to mirror block 22, continually provides temperature information to circuit board 45 (see FIG. 9). Upon detecting that frost or dew has formed on polished mirror 23, circuit board 45 records the temperature at which the frost or dew was detected. Thermoelectric module 21 is then raises the temperature of mirror block 22 and polished mirror 23 until the frost or dew evaporates, thereby increasing the amount of light received by photo-transistor or optical detector 42, which registers the increased amount of light being received, whereupon thermoelectric module 21 begins cooling mirror block 22 and polished mirror 23 again, as described further below with respect to a software controller for controlling the operation of the chilled mirror hygrometer.

In examples including only a first photo-transistor or optical detector 42, as shown in FIG. 10, for example, the photo-transistor or optical detector may require a means for differentiating between the light being emitted by first LED 41 and second LED 43. In some examples, LEDs 41 and 43 may be controlled by a software controller that only activates one LED at a time, allowing photo-transistor or optical detector 42 to observe the light emitted by each LED separately. In such examples, the software controller may be programmed to sequence the power supplied to the LEDs such that photo-transistor or optical detector 42 may record three or more distinct optical signals. In a first interval of the software controller, first LED 41 may be activated, thereby allowing light from LED 41 to pass through sample chamber 66, and be reflected off of the surface of chilled mirror 22. The light may then be reflected back towards photo-transistor or optical detector 42. There, the light intensity for the first interval may be observed and stored in memory. In a second interval, the power supplied to first LED 41 may be shut off, while the power supplied to second LED 43 may be activated, thereby allowing light to pass through shutter 46 and received by photo-transistor or optical detector 42. There, the light intensity for the second interval may be observed and stored in memory. In a third interval, the software controller may cause the power supplied to both first LED 41 and second LED 43 to be switched off, thereby allowing photo-transistor or optical detector 42 to observe the ambient background light caused by any sources other than first LED 41 and/or second LED 43. During the third interval the photo-transistor or optical detector 42 may observe the light intensity and store the reading in memory.

During an initial calibration procedure, such as an ABC Cycle or PACER Cycle, the software controller may be further programmed to heat the polished mirror by reversing the current through thermoelectric module 21. As the temperature of the polished mirror 23 continues to rise, the software controller may continue to run all three measurement intervals, such that any residual condensate from a previous measurement cycle may be detected, and a dry surface of polished mirror 23 may be indicated when the light measurement for the second interval is unchanged across two or more measurement cycles.

The optical levels measured from a dry polished mirror 23 represents the baseline optical levels for the device. The light measurement taken at interval 1 represents the light reflected from a dry polished mirror 23. The light measurement taken at interval 2 represents the light distortion caused by the current temperature and atmospheric conditions of the air currently being sampled. The light measurement taken at interval 3 represents the ambient background light measurement. In some examples, the software controller may be further programmed to process the baseline optical measurements by subtracting the interval 3 measurement from both intervals 1 and 2, thereby removing the unsynchronized background signal and enhancing the signal to noise ratio (SNR) of the optical detection. The software controller then processes the modified interval 1 & 2 signals ratiometrically and normalizes them to a value of 1, which represents the reference value against which future readings will be compared. In an "ideal" instrument, this reference level would remain stable over time and temperature. In a practical instrument, this is rarely the case. Examples of the invention mitigate the effects of temperature change over time by allowing the device to continually read the effect of ambient temperature change on photo detection. Because the measured quantity is a ratio of the measurements from intervals 1 and 2, changes in the detector sensitivity due to changes in temperature are nearly eliminated. Also, because first LED 41 and second LED 43 are both in the same thermal environment, as well as excited with equal values of current, these components will have consistent variations resulting from changes in ambient air temperature. Therefore, any effect from temperature change will be expressed substantially equally, thus cancelling each other out during ratiometric processing.

Figure 11:
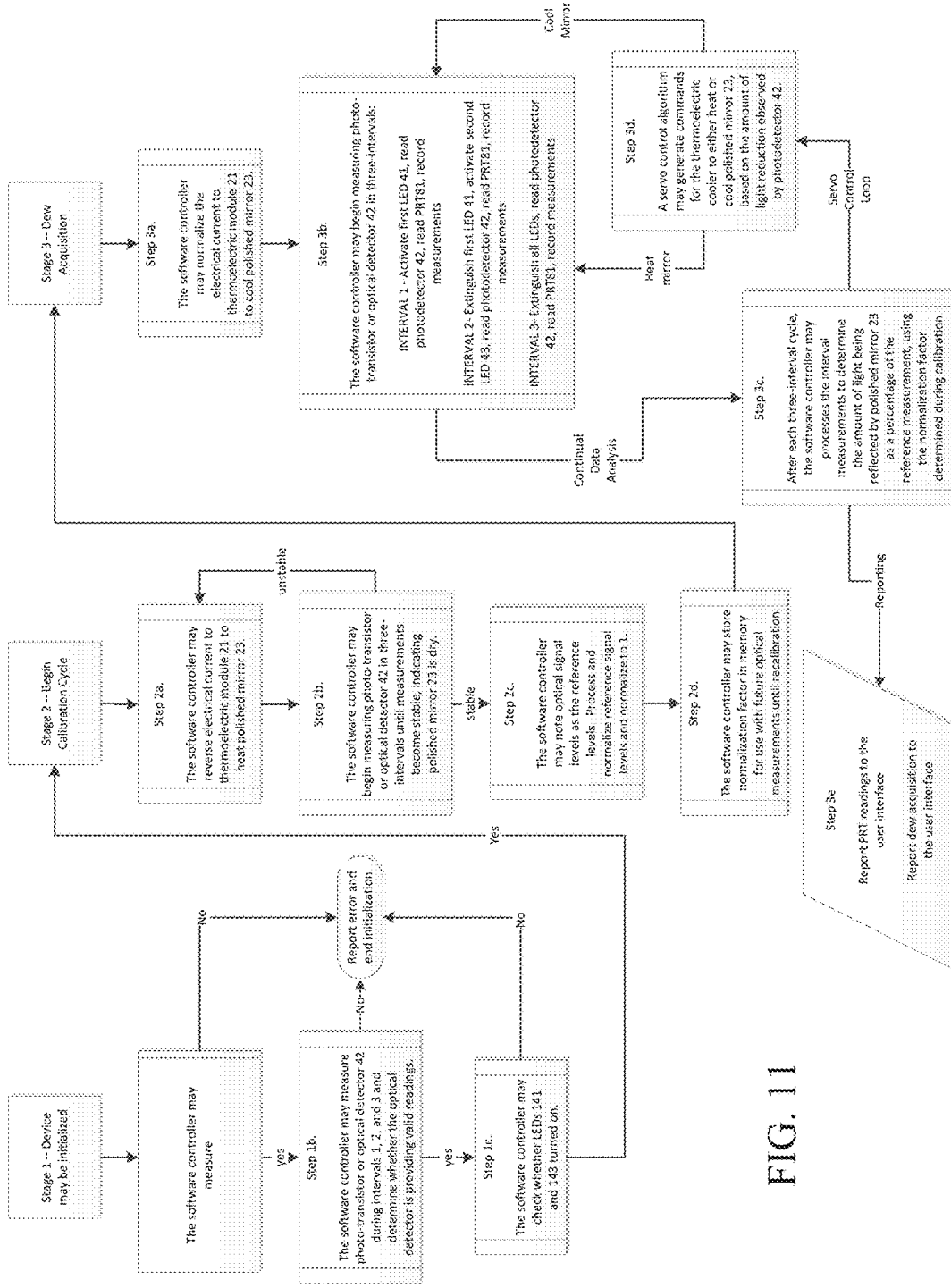
FIG. 11 is a flowchart showing the processes that may be attributable to a software controller for a chilled mirror hygrometer

FIG. 11 provides a flowchart, detailing the operation of a software controller in some examples of the invention. For example, during a first stage, the device may be initialized by the software controller. At step 1a, the software controller may send a signal to PRT 81 to take one or more measurements in order to determine whether the software controller is receiving a valid signal from PRT 81. At step 1b, the software controller may send a signal to optical detector 42 to take one or more measurements from the optical detector during a first, second, and third measurement interval (as described above), in order to determine whether the software controller is receiving a valid signal from optical detector 42. At step 1c, the software controller may send a signal to first LED 141 and/or second LED 142 to activate, while also sending one or more signals to optical detector 42 to measure the change in light intensity in order to determine whether first LED 141 and/or second LED 142 is properly activating. If an invalid signal is received by the software controller at any of steps 1a-1c, the software controller will report the error to the user interface, and end device initialization.

At a second stage, the software controller may undertake a calibration cycle in order to re-calibrate the device, in an ABC or PACER cycle, as is known to one of ordinary skill in the art. For example, at step 2a, the software controller may send a signal to thermoelectric module 21 to reverse its electrical current, thereby heating polished mirror 23. At step 2b, the software controller may begin measuring optical detector 42 in a first, second, and third interval (as described above), until the measurement becomes stable, indicating that polished mirror 23 may be dry. At step 2c, the software controller notes the stable measurement of optical detector 42 as the reference measurement and normalizes the measurement to a value of 1, thereby determining a normalization factor. At step 2d, the normalization factor is stored in memory for use in normalizing future optical measurements until the next recalibration.

At a third stage, the software controller may enter a "dew acquisition" or measurement phase. At step 3a, the software controller may send a signal to thermoelectric module 21 to normalize the electrical current and thereby begin cooling polished mirror 23. At step 3b, the software controller may send a series of signals to first LED 41, LED 43, PRT 81, and/or photodetector 42, in order to begin measuring polished mirror 23 in three intervals, as described above and as shown in step 3b of FIG. 11. The software controller may be configured to record the measurements received from photodetector 42 and PRT 81 after each measurement interval for data analysis during step 3c.

At step 3c, the software controller may be programmed to conduct continual data analysis of the measurements received from photodetector 42 and/or PRT 81 after each three-measurement cycle. After each cycle, the software controller may be programmed to analyze the data to determine the amount of light being reflected by polished mirror 23 as a percentage of the light reflected during the reference measurement, as established during the second (calibration) stage. To do so, the software controller may subtract the measurement observed from photodetector 42 during the third interval (background light reading), from the measurement recorded for both intervals 1 (polished mirror reading), and 2 (ambient air distortion reading). As explained above, subtracting the interval 3 measurement from both intervals 1 and 2, removes the unsynchronized background signal and enhances the SNR of the optical detection. The software controller then processes the modified interval 1 & 2 signals ratiometrically to determine a ratio of the polished mirror reading to the background ambient air reading. This value may then be normalized using the normalization factor determined and stored by the software controller during steps 2c-2d. The software controller may further be configured to determine whether dew and/or frost has begun to form on the polished mirror 23 surface by evaluating the current, normalized reading. If the light reduction on the polished mirror is greater than a specified amount (e.g. greater than 15%), then the software controller reports the temperature reading of PRT 81 taken during interval 1 and also reports that dew and/or frost has been acquired on the surface of polished mirror 23 to the user interface.

At step 3d, the software controller maybe configured to determine whether to instruct thermoelectric module 21 heat or cool polished mirror 23 in order to maintain or acquire the dew or front on polished mirror 23. To do so, the software controller may be programmed with a servo control algorithm as is known to one of ordinary skill in the art. A servo control algorithm may generate commands for thermoelectric module 21 to either to increase or decrease its temperature, and the desired rate of cooling or heating, based on the reduction in light observed by the software controller in step 3c. For example, in some cases, dew or frost is deemed to be acquired on polished mirror 23 when the light is observed to have been reduced between 15% and 50% from the reference measurement. In such instances, the servo control algorithm may instruct the thermoelectric module 21 to continue rapid cooling when the reduction in observed light is less than 15%. On the other hand, a servo control algorithm may instruct thermoelectric module 21 to rapidly heat polished mirror 23 when the reduction in observed light is greater than 50%, which indicates excess frost or condensation. When the reduction in observed light is between 15% and 50% (i.e. dew or frost has been acquired), a servo control algorithm may maintain the frost/dew point by sending appropriate heating/cooling instructions to thermoelectric module 21 using a proportional integral derivative control loop, as is known to one of ordinary skill in the art.

At step 3e, the software controller may be configured to report the measurements of PRT 81 for each measurement cycle. The software controller may further be configured to report dew/frost acquisition—i.e. whether the software controller has determined that dew or frost has formed on the surface of polished mirror 23. As stated above, in some examples, a software controller may determine that dew or frost has formed on polished mirror 23 when the observed reduction in reflected light from polished mirror 23 is between 15% and 50% and relatively stable. For example, a series of measurements may be deemed stable when the software controller observes a standard deviation between a series of measurement cycles that is below a desired standard deviation.

In some examples platinum resistance thermometer 81 (from thermoelectric module 21), PRT 83 (from mirror block 22) and PRT 40 (which measures the temperature of ambient air), may all be connected to circuit board 45, as shown, for example, in FIG. 9 to allow a software controller to take measurements from the various PRTs, as needed. Photo-transistor or optical detector 42 may also be connected to circuit board 45, as shown for example in FIGS. 12A and 12B and may be stored within circuit 100. Thus, in some examples, circuit board 45 is configured to receive analog signals from each of PRT 81, PRT 83, PRT 40, and photo-transistor or optical detector 42. In some examples, these same analog signals may be sent from circuit board 45 or circuit 100 to electrical housing 1 via one or more wires. However, it may be advantageous, in some examples, to convert these and potentially other analog signals into a single digital signal locally, at circuit board 45, before transmitting them to electrical housing 1. Processing the analog signals at board 45 and converting them into a single digital signal cuts down on the number of wires, and therefore the space required, to transmit the information gathered by the chilled mirror hygrometer for further processing. Furthermore, because the analog signals are being converted within the wand portion, itself, electrical housing 1 and wand portion 10 are more modular and therefore may be more readily repaired with replacement components.

Analog signals may be converted to a digital signal using any suitable technique known to one of ordinary skill in the art. In some examples, analog signals may be received in the form of electrical current. The current may then be amplified by a transimpedance amplifier (TIA) 102, which takes the low level current supplied by each of PRT 81, PRT 83, PRT 40, and/or photo-transistor or optical detector 42 and outputs of a voltage that may then be read by an analog-digital converter in a manner known to one of ordinary skill in the art. The converted digital signal may include information relating to temperature reports from one or more PRTs (including ambient temperature readings and polished mirror temperature readings), as well as a condensation state signal indicating that polished mirror 23 has acquired either dew or frost. Once converted, the digital signal may be passed to electronic housing 1 for further transmission to an external user interface.

Additional components and circuitry may be located within electronic housing 1, including electronic components for supplying electricity to thermoelectric module 21. In some examples, separate circuitry for operating the servo control algorithm (described above) may be located in electronic housing 1 as well. Electronic housing 1 may also house digital outputs for supplying digital information to and receiving information and user commands for an external user interface. In some examples, a RS232 connection located in housing 1 may provide the necessary connection to an external user interface. In some examples, a chilled mirror hygrometer may be coupled to other industrial applications for automatically controlling dew or frost point-sensitive equipment. In such cases, electronic housing 1 may include additional digital or analog outputs for controlling such industrial equipment. In some examples, electronic housing 1 may include two analog 4-20 milli-amp outputs for this purpose. In yet further examples, electronic housing 1 may also include additional circuitry programmed to calculate additional moisture values based on the fundamental measurements supplied by the chilled mirror hygrometer (i.e. dew point and air temperature). Additional moisture values may include vapor pressure, mixing ratio, latent heat, percent saturation, relative humidity, or absolute humidity. These measurements are a based on the fundamental measurements of dew point and ambient temperature and therefore may be calculated by an external user interface or may be calculated by additional circuitry within electronic housing 1 and supplied to a user interface along with the dew/frost point and temperature information.

It will be apparent to those skilled in the art that various modifications and variations can be made in the method and system of the disclosed subject matter without departing from the spirit or scope of the disclosed subject matter. Thus, it is intended that the disclosed subject matter includes modifications and variations that are within the scope of the appended claims and their equivalents.

What is claimed is:

1. A chilled mirror hygrometer comprising:
   a thermoelectric module;
   a polished mirror;
   two light emitting diodes;
   a single photo-transistor or optical detector;
   a wand portion and an electrical housing, said wand portion having a distal end located away from said electrical housing and a proximal end adjacent to said electrical housing; and
   one or more platinum resistance thermometers,
   wherein said wand portion further comprises two or more cylindrical housings, said housings being rotatably connected; and
   wherein said two or more cylindrical housings may be rotated to align one or more holes or openings in said two or more cylindrical housings and said aligned holes or openings provide access to a sample chamber, said sample chamber being located between at least one of said two light emitting diodes and said polished mirror surface.

2. The chilled mirror hygrometer according to claim 1, further comprising a fan.

3. The chilled mirror hygrometer according to claim 1, wherein air samples may be exposed to said sample chamber near said distal end of said wand portion when said holes or openings in said two or more cylindrical housings are misaligned.

4. The chilled mirror hygrometer according to claim 2, wherein said fan is actuated during a calibration procedure.

5. The chilled mirror hygrometer according to claim 2, wherein said fan is actuated when the chilled mirror hygrometer is sampling an air sample.

6. The chilled mirror hygrometer according to claim 1, wherein air samples may be exposed to said sample chamber by passing through said holes or openings in said two or more cylindrical housings when said holes or openings in said two or more cylindrical housings are aligned.

7. The chilled mirror hygrometer according to claim 6, further comprising a plug, which may be inserted into said wand portion so that said sample chamber is isolated from said distal end of said wand portion.

8. The chilled mirror hygrometer according to claim 1, further comprising a processor programmed with a software controller for taking air sample measurements in at least three intervals, including:
   a first interval, wherein both of said two light emitting diodes are deactivated and said photo-transistor or optical detector is measured;
   a second interval, wherein a first of said two light emitting diodes is activated and said photo-transistor or optical detector is measured; and a third interval, wherein a second of said two light emitting diodes is activated and said photo-transistor or optical detector is measured.

9. A chilled mirror hygrometer comprising:

an air sampling chamber, comprising a polished mirror, a first light source, a second light source, and an optical detector;

a wand portion and an electrical housing, said wand portion having a distal end located away from said electrical housing and a proximal end adjacent to said electrical housing;

one or more platinum resistance thermometers;

a thermoelectric module disposed adjacent said polished mirror; and a processor programmed with a software controller for taking air sample measurements in at least three intervals, including:
  a first interval, wherein both of said first and said second light sources are deactivated and said optical detector is measured;
  a second interval, wherein the first light source is activated and said optical detector is measured; and
  a third interval, wherein the second light source is activated and said optical detector is measured, wherein said wand portion further comprises two or more cylindrical housings, said housings being rotatably connected; and wherein said two or more cylindrical housings may be rotated to align one or more holes or openings in said two or more cylindrical housings and said aligned holes or openings provide access to a sample chamber, said sample chamber being located between at least one of said first light source or said second light source and said polished mirror.

10. The chilled mirror hygrometer of claim 9, wherein said first light source is aimed at said polished mirror, such that at least a portion of light emitted from said first light source will be received at said optical detector.

11. The chilled mirror hygrometer of claim 10, wherein said second light source is aimed at said optical detector, such that at least a portion of light emitted from said second light source will be received at said optical detector.

12. The chilled mirror hygrometer of claim 11, wherein said first and said second light sources are light emitting diodes.

13. The chilled mirror hygrometer of claim 12, wherein said processor is further programmed to measure and record a temperature from one or more of said one or more thermometers during at least one of said first interval, said second interval, and/or said third interval.

14. The chilled mirror hygrometer of claim 13, wherein said processor is further configured to perform a calibration procedure.

15. The chilled mirror hygrometer of claim 14, wherein said calibration procedure is a PACER cycle or an ABC cycle.

16. The chilled mirror hygrometer of claim 14, wherein said processor is further configured to actuate a fan, disposed within the chilled mirror hygrometer, during said calibration procedure.

* * * * *